(12) United States Patent
Drumheller et al.

(10) Patent No.: US 8,048,500 B2
(45) Date of Patent: Nov. 1, 2011

(54) COMPOSITE SELF-COHERED WEB MATERIALS

(75) Inventors: Paul D. Drumheller, Flagstaff, AZ (US);
Ted R. Farnsworth, Flagstaff, AZ (US);
Charles Flynn, Flagstaff, AZ (US);
Byron K. Hayes, Flagstaff, AZ (US);
Charles F. White, Camp Verde, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 12/389,232

(22) Filed: Feb. 19, 2009

(65) Prior Publication Data

US 2009/0202611 A1 Aug. 13, 2009

Related U.S. Application Data

(63) Continuation of application No. 11/192,743, filed on Jul. 29, 2005, now abandoned.

(51) Int. Cl.
*A61F 2/02* (2006.01)
*B32B 1/08* (2006.01)
*B32B 23/00* (2006.01)
*B32B 25/02* (2006.01)

(52) U.S. Cl. .................. 428/34.6; 428/36.5; 623/11.11; 623/23.72; 623/23.73; 623/23.74; 623/23.75; 623/23.76

(58) Field of Classification Search ........................ None
See application file for complete search history.

(56) References Cited

U.S. PATENT DOCUMENTS

| | | | |
|---|---|---|---|
| 3,047,444 A | 7/1962 | Hardwood |
| 3,772,417 A | 11/1973 | Vogt |
| 4,349,500 A | 9/1982 | Yazawa et al. |
| 5,092,884 A | 3/1992 | Devereux et al. |
| 5,098,779 A | 3/1992 | Kranzler et al. |
| 5,141,522 A | 8/1992 | Landi |
| 5,238,618 A | 8/1993 | Kinzer |
| 5,244,482 A | 9/1993 | Hassenboehler, Jr. et al. |
| 5,321,109 A | 6/1994 | Bosse et al. |
| 5,328,653 A | 7/1994 | Hyde et al. |
| 5,466,517 A | 11/1995 | Eschwey et al. |
| 5,468,253 A | 11/1995 | Bezwada et al. |
| 5,670,161 A | 9/1997 | Healy et al. |
| 5,685,757 A | 11/1997 | Kirsch et al. |
| 5,730,821 A | 3/1998 | Joest et al. |
| 5,814,569 A | 9/1998 | Suzuki et al. |
| 5,824,335 A | 10/1998 | Dorigatti |
| 5,830,810 A | 11/1998 | Cohen et al. |
| 5,833,787 A | 11/1998 | Ehret et al. |
| 5,851,937 A | 12/1998 | Wu et al. |
| 5,876,432 A | 3/1999 | Lau et al. |

(Continued)

FOREIGN PATENT DOCUMENTS

EP 0 647 734 4/1995

(Continued)

*Primary Examiner* — Jennifer Chriss
*Assistant Examiner* — Camie Thompson
(74) *Attorney, Agent, or Firm* — Andrea W. Burke

(57) ABSTRACT

The present invention is directed to implantable bioabsorbable non-woven self-cohered web materials having a high degree of porosity. The web materials are very supple and soft, while exhibiting proportionally increased mechanical strength in one or more directions. The web materials often possess a high degree of loft. The web materials can be formed into a variety of shapes and forms suitable for use as implantable medical devices or components thereof.

49 Claims, 21 Drawing Sheets

U.S. PATENT DOCUMENTS

| | | | |
|---|---|---|---|
| 5,932,316 A | 8/1999 | Cree et al. | |
| 6,025,458 A | 2/2000 | Lipinsky et al. | |
| 6,075,180 A | 6/2000 | Sharber et al. | |
| 6,093,792 A | 7/2000 | Gross et al. | |
| 6,113,624 A | 9/2000 | Bezwada et al. | |
| 6,113,640 A | 9/2000 | Tormala et al. | |
| 6,136,018 A | 10/2000 | Roby et al. | |
| 6,165,202 A | 12/2000 | Kokish et al. | |
| 6,165,217 A * | 12/2000 | Hayes | 623/11.11 |
| 6,171,338 B1 | 1/2001 | Talja et al. | |
| 6,267,782 B1 | 7/2001 | Ogle et al. | |
| 6,287,499 B1 | 9/2001 | Roby et al. | |
| 6,303,697 B1 | 10/2001 | Yuan et al. | |
| 6,309,423 B2 * | 10/2001 | Hayes | 623/23.75 |
| 6,328,765 B1 | 12/2001 | Hardwick et al. | |
| 6,338,814 B1 | 1/2002 | Hills | |
| 6,500,464 B2 | 12/2002 | Ceres et al. | |
| 6,511,748 B1 | 1/2003 | Barrows | |
| 6,514,292 B1 | 2/2003 | Atala | |
| 6,583,232 B1 | 6/2003 | Brown | |
| 6,596,296 B1 | 7/2003 | Nelson et al. | |
| 6,637,128 B2 | 10/2003 | Kuroiwa et al. | |
| 6,645,618 B2 | 11/2003 | Hobbs et al. | |
| 6,685,956 B2 | 2/2004 | Chu et al. | |
| 6,689,374 B2 | 2/2004 | Chu et al. | |
| 6,713,011 B2 | 3/2004 | Chu et al. | |
| 6,746,685 B2 | 6/2004 | Williams | |
| 6,759,431 B2 | 7/2004 | Hunter et al. | |
| 6,770,356 B2 | 8/2004 | O'Donnell et al. | |
| 6,787,493 B1 | 9/2004 | Nagaoka et al. | |
| 6,824,372 B2 | 11/2004 | Berrigan et al. | |
| 6,855,743 B1 | 2/2005 | Gvozdic | |
| 6,896,687 B2 | 5/2005 | Dakov | |
| 6,902,729 B2 | 6/2005 | Presnell et al. | |
| 6,911,212 B2 | 6/2005 | Gertzman et al. | |
| 6,913,626 B2 | 7/2005 | McGhan | |
| 6,916,752 B2 | 7/2005 | Berrigan et al. | |
| 6,917,400 B2 | 7/2005 | Nakamura et al. | |
| 6,918,929 B2 | 7/2005 | Udipi et al. | |
| 6,944,968 B2 | 9/2005 | Cleary et al. | |
| 6,964,658 B2 | 11/2005 | Ashby et al. | |
| 7,105,018 B1 | 9/2006 | Yip et al. | |
| 2002/0016626 A1 | 2/2002 | Dimatteo et al. | |
| 2002/0160033 A1 | 10/2002 | Caplice et al. | |
| 2003/0034585 A1 | 2/2003 | Locher et al. | |
| 2003/0082977 A1 | 5/2003 | Kuroiwa et al. | |
| 2003/0088924 A1 | 5/2003 | Bolick | |
| 2004/0010320 A1 | 1/2004 | Huckle et al. | |
| 2004/0028655 A1 * | 2/2004 | Nelson et al. | 424/93.2 |
| 2004/0126405 A1 | 7/2004 | Sahatjian et al. | |
| 2004/0167606 A1 | 8/2004 | Chouinard | |
| 2004/0215322 A1 | 10/2004 | Kerr | |
| 2005/0165447 A1 | 7/2005 | Crawley et al. | |
| 2005/0187605 A1 | 8/2005 | Greenhalgh et al. | |
| 2007/0027550 A1 | 2/2007 | Farnsworth et al. | |
| 2007/0027552 A1 | 2/2007 | Farnsworth et al. | |
| 2007/0027554 A1 | 2/2007 | Biran et al. | |

FOREIGN PATENT DOCUMENTS

| | | |
|---|---|---|
| EP | 0 667 119 | 8/1995 |
| EP | 0 835 894 | 4/1998 |
| EP | 1 520 525 | 4/2005 |
| WO | 9210218 | 6/1992 |
| WO | 00/32749 | 6/2000 |
| WO | 2004/064686 | 8/2004 |
| WO | 2005/046526 | 5/2005 |
| WO | 2007/015961 | 2/2007 |
| WO | 2007/015970 | 2/2007 |
| WO | 2007/015973 | 2/2007 |
| WO | 2007/015974 | 2/2007 |
| WO | 2007/015986 | 2/2007 |

* cited by examiner

COMPOSITE SELF-COHERED WEB MATERIALS

CROSS-REFERENCE TO RELATED APPLICATIONS

This is a continuation application of application Ser. No. 11/192,743 filed Jul. 29, 2005 now abandoned.

FIELD OF THE INVENTION

The present invention relates to implantable medical materials and devices. More particularly, the present invention is directed to implantable medical materials and devices made with bioabsorbable polymeric materials in the form of non-woven, self-cohered, filamentous webs having a high degree of porosity.

BACKGROUND OF THE INVENTION

A variety of bioabsorbable polymeric compounds have been developed for use in medical applications. Materials made from these compounds can be used to construct implantable devices that do not remain permanently in the body of an implant recipient. Bioabsorbable materials are removed from the body of an implant recipient by inherent physiological process of the implant recipient. These processes can include simple dissolution of all or part of the bioabsorbable compound, hydrolysis of labile chemical bonds in the bioabsorbable compound, enzymatic action, and/or surface erosion of the material. The breakdown products of these processes are usually eliminated from the implant recipient through action of the lungs, liver, and/or kidneys. It is recognized that in the literature "bioresorbable," "resorbable," "bioabsorbable," and "biodegradable" are terms frequently used interchangeably. "Bioabsorbable" is the preferred term herein.

Bioabsorbable polymeric compounds have been used in wound closure and reconstruction applications for many decades. Sutures are the most notable examples. Molded articles, films, foams, laminates, woven, and non-woven materials have also been produced with bioabsorbable polymeric compounds. Biologically active compositions have been releasably combined with some of these bioabsorbable compounds.

U.S. Pat. No. 6,165,217, issued to Hayes, discloses a bioabsorbable material in the form of a non-woven self-cohered web (FIGS. 1 and 1A, herein). A self-cohered non-woven web material is a spun web of continuous filaments made of at least one semi-crystalline polymeric component covalently bonded as a linear block copolymer with or blended with one or more semi-crystalline or amorphous polymeric components.

The continuous filaments are produced by selecting spinning conditions that provide a tackiness to the emerging filaments and allows them to self-cohere as solid filaments as the filaments are collected in a cohesive random pile, or web, on a collecting surface. The spun filaments are intermingled together as they are collected in the form of a porous web of self-cohered filaments. The self-cohered filaments have multiple contact points with each other within the web. The self-cohered filaments bond at the contact points without need for requisite addition of supplementary adhesives, binders, adhesive adjuncts (e.g., solvents, tackifier resins, softening agents), or post extrusion melt processing. The self-cohered filaments of the preferred embodiment polyglycolide:trimethylene carbonate (PGA:TMC) non-woven web are between 20 microns and 50 microns in diameter. According to Hayes, these self-cohered non-woven webs possess volume densities (also reported as apparent densities) that indicate percent porosity to be in a range between approximately forty (40) and eighty (80). If the potentially semi-crystalline web is preserved in a thermodynamically unstable (metastable), homogeneous (microphase disordered), substantially phase miscible, amorphous state of limited crystallinity, the web is malleable and can be ready conformed or molded into a desired shape. That shaped form can then be preserved through its conversion into a more ordered, thermodynamically stable, at least partially phase immiscible semi-crystalline state. This irreversible (short of complete remelting and reformation of the formed web structures) conversion from a prolonged amorphous (i.e., disordered state of miscibility) condition into an ordered semi-crystalline state is typically provided by the chain mobility present in the rubbery state existing between the melt temperature and that of the order-disorder transition temperature ($T_{odt}$), the temperature above which the transition from disorder to order can proceed. Alternatively, solvents, lubricants, or plasticizing agents, with or without their combination with heat, can be used to facilitate chain mobility, and rearrangement of the constituent polymer chains into a more ordered condition. The chemical composition of the self-cohered filaments can be chosen so the resultant web is implantable and bioabsorbable.

Hayes describes the self-cohered non-woven web material as possessing a degree of porosity variable based on fiber deposition density and any subsequent compression. Hayes also describes the ability of the planar web in the malleable unstable amorphous condition to be shaped into a virtually unlimited array of forms, the shapes of which can be retained through subsequent crystallization. However, Hayes does not indicate an unset web of the self-cohered filaments which can serve as a precursor web material for additional stretch processing to increase web porosity prior to annealing. Nor does Hayes teach a self-cohered non-woven web material having a significant population of continuous filaments with a cross-sectional diameter less than twenty (20) microns. In the absence of additional processing of a precursor web material according to the present invention, the self-cohered non-woven web material of Hayes would not have increased molecular orientation in the self-cohered filaments of the web sufficient to provide a birefringence value greater than 0.050.

A non-woven self-cohered web material having high porosity and small filament diameter would have proportionally increased mechanical strength in one or more directions. Despite increased mechanical strength, such a high porosity non-woven self-cohered web material would deliver more loft, suppleness, drapability, conformability, and tissue compliance than a web material made according to Hayes.

For non-implantable applications, a non-woven self-cohered web having a high degree of porosity could be used to releasably attach implantable devices and materials to a delivery apparatus. Combining a population of oriented filaments with an increased internal void volume within which the oriented filament can move would imbue such a material with a degree of elasticity or resiliency.

In addition to these and other improvements in such a web material, a more porous bioabsorbable web material would provide opportunities to combine other components with the web. The components could be placed on surfaces of the filaments. The components could also be placed within void spaces, or pores, between the filaments. The components could be bioabsorbable or non-bioabsorbable. The components, in turn, could releasably contain useful substances.

There is a need, therefore, for a synthetic bioabsorbable, non-woven, self-cohered polymeric web material having a high degree of porosity with increased mechanical strength, loft, suppleness, drapability, conformability, and tissue compliance.

SUMMARY OF THE INVENTION

The present invention is directed to synthetic bioabsorbable, non-woven, self-cohered polymeric web materials having a high degree of porosity. The highly porous web materials are mechanically strong and have a high degree of loft, suppleness, drapability, conformability, and tissue compliance. In some embodiments, the present invention exhibits elastic properties. The invention is suitable for use as an implantable medical device or a component of a medical device. The invention is also suitable for use in many instances as a thrombogenic agent at a site of bleeding or aneurysm formation.

These properties are imparted to the present invention by drawing, or stretching, an unannealed, self-cohered, precursor web material in at least one direction at a particular rate and stretch ratio under defined conditions. Stretching is followed preferentially by heat-setting and cooling under full or partial restraint.

Self-cohered, precursor web materials have filaments attached to one another at multiple contact points (FIGS. 1 and 1A). During processing, the filaments are kept secured together by the self-cohering contact points. As the self-cohered filaments are stretched, the filaments elongate and become smaller in cross-sectional diameter (FIGS. 2-4A, and 6-7). As the filaments become finer, increased void space is formed between the filaments (Table 12). The as-stretched structure is then "set" or annealed, either completely or partially under restraint, to induce at least partial phase immiscibility and subsequent crystallization. The finer filaments and increased void space generated within the web material are responsible for many of the improved characteristics of the present invention.

A convenient metric for quantifying the void space of a porous web material is the percent porosity of the finished web material. The percent porosity compares the density of an unprocessed starting compound with the density of a finished porous web material. The stretched, self-cohered, continuous filament nonwoven web materials of the present invention are greater than ninety percent (90%) porous. In the present invention, the increased porosity imparted to the web is defined as the void space provided within the external boundaries of the stretched self-cohering web, absent the inclusion of any fillers or other added components that may effectively reduce the available porosity.

The present invention can include additional compositions placed on and/or within the polymeric components of the web material. Additional compositions can also be placed in void spaces, or pores, of the web material. The compositions can include useful substances releasably contained thereby. Preferred compositions for placement in void spaces and surfaces of the present invention are hydrogel-based materials.

In one embodiment, the present invention is an implantable article comprising melt-formed continuous filaments intermingled to form a porous web wherein said filaments are self-cohered to each other at multiple contact points, wherein said filaments comprise at least one semi-crystalline polymeric component covalently bonded to or blended with at least one amorphous polymeric component, wherein the filaments possess partial to full polymeric component phase immiscibility when in a crystalline state, and a hydrogel material placed on at least one of said filaments.

In another embodiment, the present invention is an implantable article comprising melt-formed continuous filaments intermingled to form a porous web wherein said filaments are self-cohered to each other at multiple contact points, wherein said filaments comprise a first semi-crystalline polymeric component covalently bonded to or blended with at least one additional semi-crystalline polymeric component, wherein the filaments possess partial to full polymeric component phase immiscibility when in a crystalline state, and a hydrogel material placed on at least one of said filaments.

These and other features of the present invention, as well as the invention itself, will be more fully appreciated from the drawings and detailed description of the invention.

DETAILED DESCRIPTION OF THE INVENTION

Figure 1:
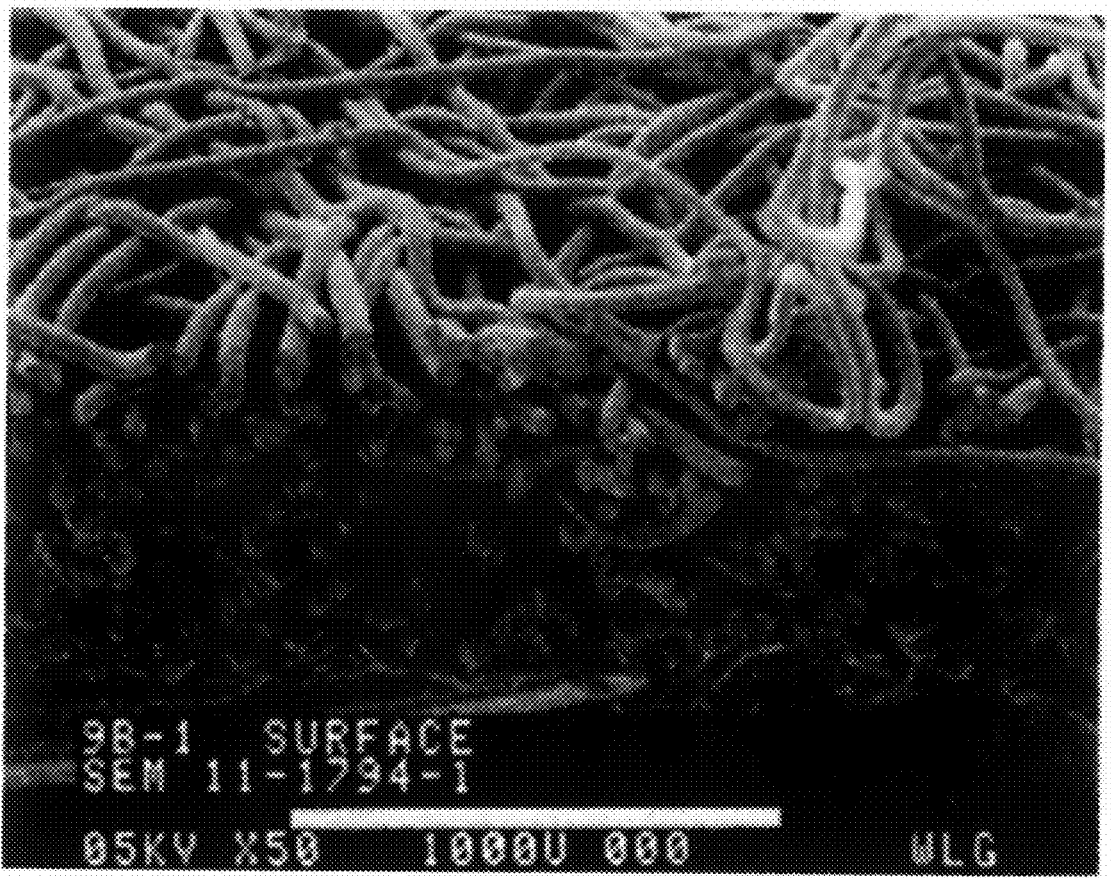
FIG. 1 is a scanning electron micrograph (SEM) of a self-cohered web material of the prior art.
Figure 1A:
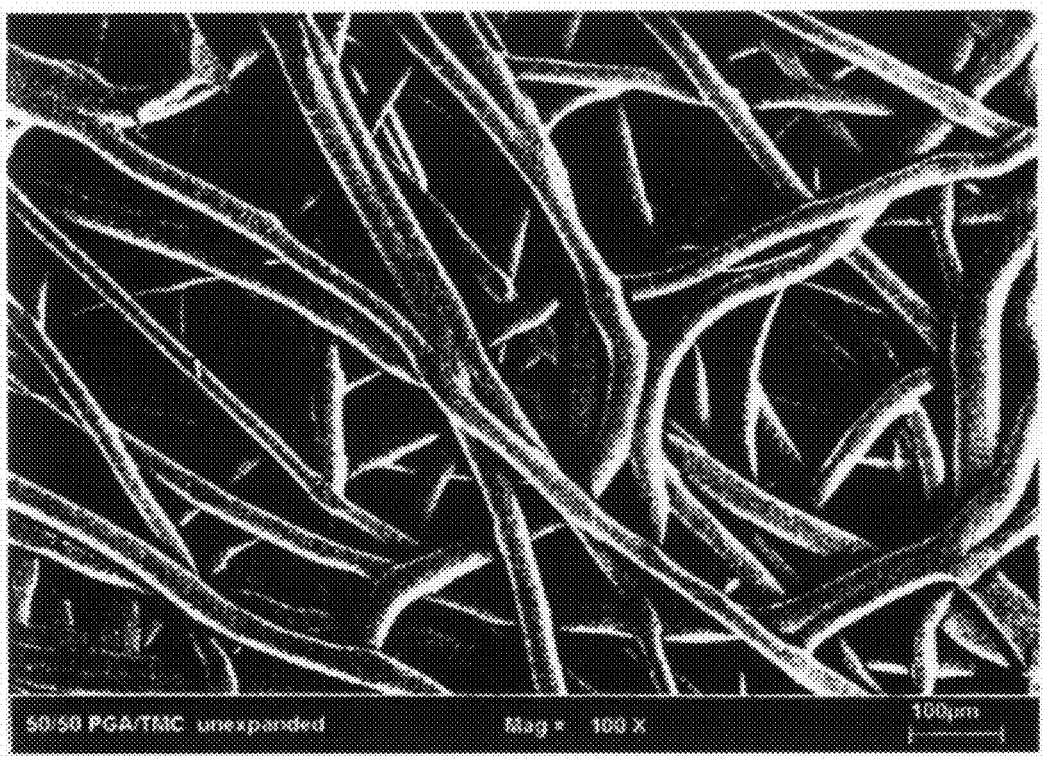
FIG. 1A is a scanning electron micrograph (SEM) of a self-cohered web material of the prior art.

The present invention is directed to bioabsorbable nonwoven, self-cohered, polymeric web materials having a high degree of porosity. The high degree of porosity imparts many desirable features to the invention. These features include loft, suppleness, drapability, conformability, and tissue compliance. Many of these highly porous materials exhibit substantial mechanical strength. The highly porous web materials of the present invention can be used as implantable medical devices or components thereof. When implanted, the highly porous bioabsorbable web materials of the present invention are removed from the body of an implant recipient by inherent physiological processes of the implant recipient.

The highly porous web materials of the present invention are made by stretching an unannealed, non-woven, self-cohered, unstretched precursor web material in one or more directions, sequentially or simultaneously, followed by annealing of the polymeric constituents of the stretched web material with heat and/or appropriate solvents. The precursor web material is made of continuous filaments formed from semi-crystalline multi-component polymeric systems which, upon the achievement of an equilibrium state, possess some evidence of phase immiscibility of the system's constituent polymeric components. The ability of the precursor web material to initially self-cohere after solidification from the melt is believed to be the result of a comparatively reduced rate of crystallization. The reduced rate of crystallization preserves the melt's substantially homogenous amorphous non-crystalline phase mixed condition within the solidified quenched filamentous web until such a time that it can come into physical contact with other portions of the continuous filament sustained in a similar amorphous condition of limited crystallization. As portions of the continuous filaments contact each other at multiple points in the precursor web material, the filaments are bonded together at the contact points in a solidified state without requisite for added adhesive binders, adjuncts, or post extrusion melt processing. Continuous or discontinuous filaments connected in such a manner are considered to be "self-cohered."

Blend and copolymeric systems that exist in a state of full component miscibility within their amorphous phase, be it in a metastable or equilibrium state, are expected to display a single $T_g$ or $T_{odt}$ occurring at a temperature that is a function of the systems' composition and substantially predictable when utilizing the Fox equation. Conversely, fully immiscible multiphase amorphous systems are expected to display distinct $T_g$'s which correlate with the homopolymer analogs for each separated immiscible phase. In a partially miscible system, some crystallizable or other constituents remain miscible within the existing amorphous phase due to reasons such as steric constraints or segment inclusions. As a result, the respective $T_g$ would be shifted away from that of its non-crystallizing homopolymer analog toward a temperature reflective of the constituent ratio existing within the amorphous phase, a value which could be interpreted utilizing the Fox equation.

Similarly, non-crystallizing or amorphous inclusions within the crystalline regions of such partially miscible systems, when present in sufficient concentrations, can be expected to produce a diluent or colligative effect resulting in a depression of the melting temperature from that expected of a crystallized homopolymer analog. Such partially miscible systems would result in the depression of the observed $T_m$ while a fully phase separated system would retain a $T_m$ similar to that of the homopolymer analog.

In the present invention, the self-cohered precursor web material can be suspended in a substantially homogenous amorphous non-crystalline metastable phase mixed condition that enables the precursor web material to be stretched in one or more directions, either sequentially or simultaneously, to cause elongation and thinning of the self-cohered filaments. Stretching a precursor web material increases void space between the intermingled filaments in the web material. Though Hayes describes materials with a porosity between approximately forty and eighty percent for a finished self-cohered web made according to the teachings of U.S. Pat. No. 6,165,217, the present inventors have discovered the precursor web material can have void spaces amounting to ninety-percent (90%) of the total volume of material. This metric is expressed herein as a percent porosity, or simply "porosity." Porosity is determined as described in Example 3, herein. Finished web materials of the present invention have porosity values greater than ninety percent (90%) (Table 12).

The prolonged amorphous state present in the precursor web material during processing is attainable through the preferential selection and utilization of at least partially phase immiscible blends or block copolymers combined with a sufficiently rapid rate of cooling that substantially inhibits both full or partial microphase separation, as well as subsequent crystallization. At least partially phase immiscible blends of polymers or copolymers can be utilized, provided the polymeric mixture possesses sufficient melt miscibility to allow for its extrusion into filaments. The present invention preferentially utilizes block copolymers that can be described as diblock, triblock, or multiblock copolymers that possess at least partially phase immiscible segmental components when in a thermodynamically stable state. Phase immiscibility in the context of block copolymers is intended to refer to segmental components which, if a part of a blend of the correlating homopolymers, would be expected to phase separate within the melt.

More particularly, the current invention preferentially utilizes an ABA triblock copolymer system synthesized through a sequential addition ring opening polymerization and composed of poly(glycolide), also known as PGA, and poly(trimethylene carbonate), also known as TMC, to form a highly porous, stretched, self-cohered, non-woven bioabsorbable web material; wherein A comprises between 40 and 85 weight percent of the total weight, and wherein A is comprised of glycolide recurring units; and B comprises the remainder of the total weight and is comprised of trimethylene carbonate recurring units said material being bioabsorbable and implantable. Preferred precursor web materials are made with PGA:TMC triblock copolymers having ratios of PGA to TMC of sixty-seven percent (67%) to thirty three percent (33%) (67:33-PGA:TMC) and fifty percent (50%) PGA to fifty percent (50%) TMC (50:50-PGA:TMC). The inherent viscosity of these polymers at 30° C. in hexafluoroisopropanol (HFIP), can range from an average of 0.5 dl/g to over 1.5 dl/g, and for preferred use can range from 1.0 do/g to 1.2 dl/g. The acceptable melting point for this particular range of copolymer compositions as determined through a DSC melt peak can range from approximately 170° C. to 220° C. These copolymers' cumulative thermal exposure over time, be it from extrusion or other processing, needs to be minimized sufficiently to prevent transesterification reactions that can result in degradation of the copolymers' block structure and their correlating crystallinity and phase immiscibility characteristics.

Once a self-cohered, continuous filament precursor web material has been prepared as described herein, the web material is restrained and pre-heated above its order-disorder transition temperature ($T_{odt}$) and below its melting temperature ($T_m$) for a period of time sufficient to soften the material without inducing significant crystallization. The softened precursor web material is then subjected to stretching in one or more directions (FIGS. 2-4A). Stretching the web material in multiple directions can be performed sequentially or in a single operation. The precursor web material is stretched at a particular rate and at a particular ratio of initial dimension to final dimension.

Figure 2:
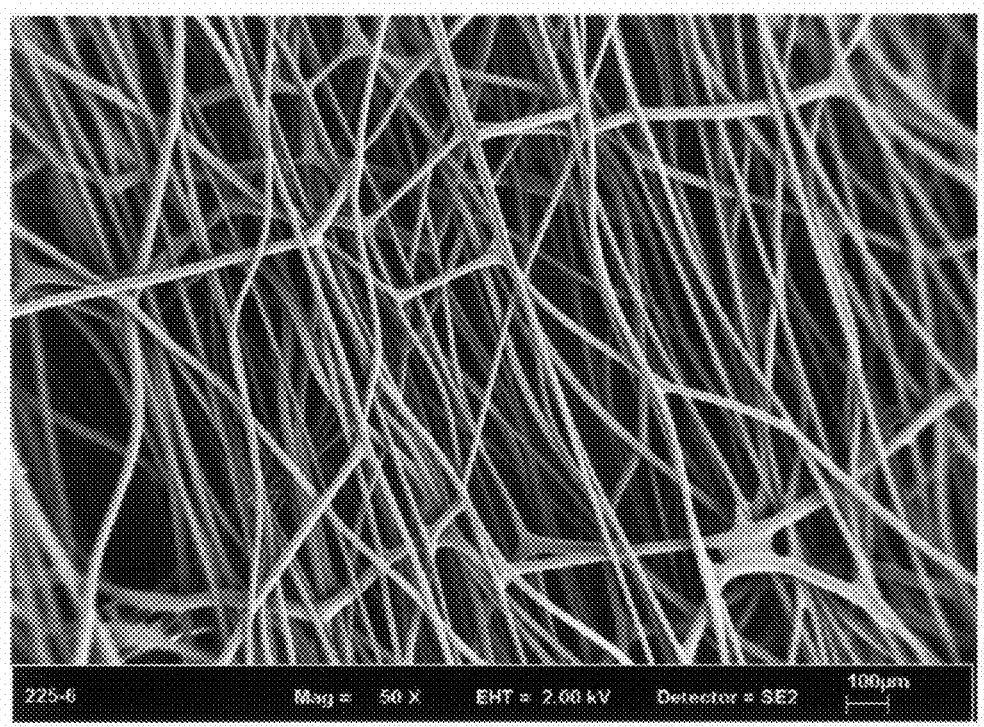
FIG. 2 is a 50× scanning electron micrograph (SEM) of an embodiment of the present invention having been stretched in a single direction.
Figure 2A:
FIG. 2A is a 100× scanning electron micrograph (SEM) of an embodiment of the present invention having been stretched in a single direction and constructed from 50-50 PGA:TMC.
Figure 3:
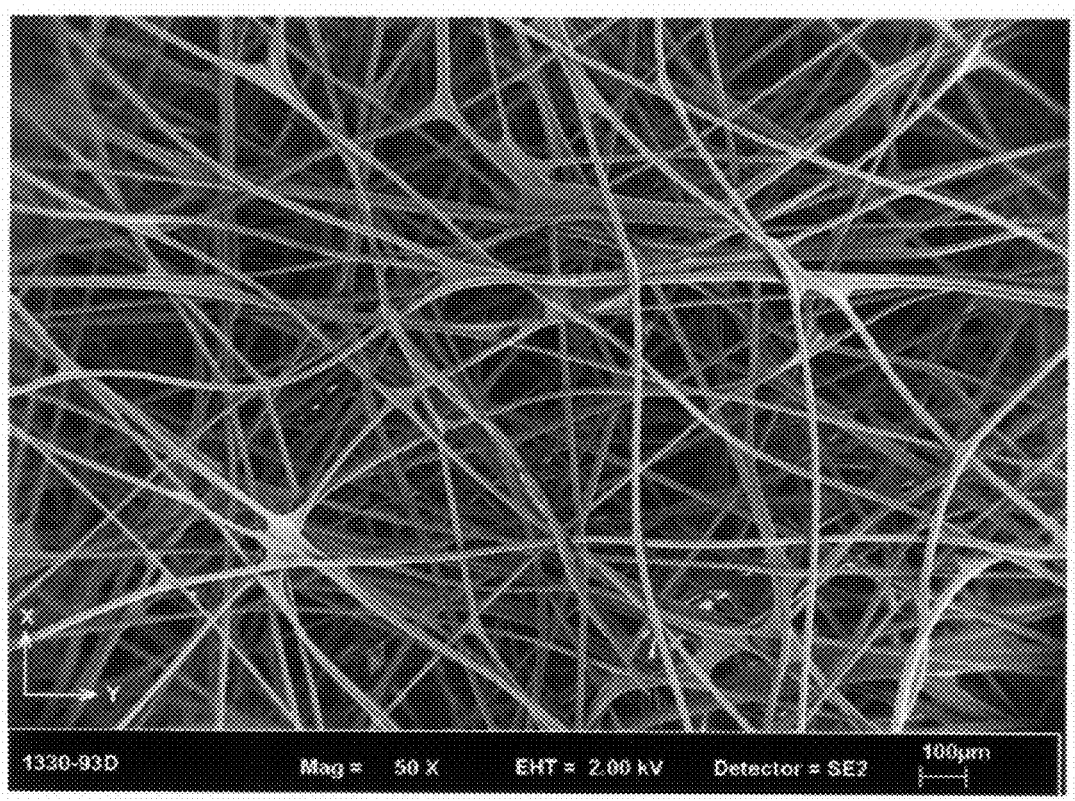
FIG. 3 is a scanning electron micrograph (SEM) of an embodiment of the present invention having been stretched in two directions substantially perpendicular to each other.

In most uni-axially stretched embodiments (FIGS. 2 and 2A), the precursor web material is stretched at rates preferably ten to fifty percent (10-50%) of the precursor web initial dimensions per second. For a given stretch rate, a precursor web material can be stretched at a ratio between two to one (2:1) and eleven to one (11:1). Preferred ratios are four to one (4:1), five to one (5:1), six to one (6:1), seven to one (7:1), eight to one (8:1), nine to one (9:1), and ten to one (10:1). Following stretching, the precursor web material is subjected to a heating step to anneal the polymeric material to induce partial to full phase separation and subsequent crytallization. The annealing step can be preformed by one of two methods.

The first annealing method requires the web be maintained at the maximum stretch at annealing conditions until the web is nearly or fully annealed. Preferred annealing conditions are 110° C. to 130° C. for 0.5 to 3 minutes, although temperatures above the order-disorder temperature ($T_{odt}$) and below the melt temperature ($T_m$), with the appropriate time adjustments, could be used.

The second annealing method is referred to herein as "partially restrained." In the method, the stretched self-cohered web material is first partially annealed while restrained at the maximum stretch. The annealing step is then completed with the restraint on the stretched web material reduced or eliminated. Preferred conditions for this method are 70° C. for 0.5 minutes for the first step (full restraint) and 120° C. for 1 to 2 minutes for the final step (reduced or no restraint).

Once annealed, the highly porous self-cohered web material is removed from the processing apparatus and prepared for use as an implantable medical device or component thereof. The advantage of the partially restrained annealing method is that it allows the stretched web to retract, typically ten to sixty percent, without an increase in fiber diameter or a reduction in porosity (see e.g., Example 9, infra) resulting in is a softer web. This softness is imparted by the curling of the fibers in the web as they retract during the final annealing step.

In most biaxially stretched embodiments (FIG. 3), the precursor web material is stretched at an approximate rate of twenty percent (20%) or thirty percent (30%) per second at 25° C. to 75° C. One preferred method is to stretch a precursor web material of 40 to 50 mg/cm$^2$ area weight at 70° C. to a stretch ratio of 3.5:1 along the x-axis (down-web) and 6.0:1 along the y-axis (transverse). By multiplying the stretch ratios of the x and y axis, this gives an area ratio of 21:1. The stretched web is partially annealed at 70° C. for 2 minutes, then released from restraints and fully annealed at 120° C. for 2 minutes. Either annealing method described above may be used for annealing biaxially stretched webs.

Figure 4:
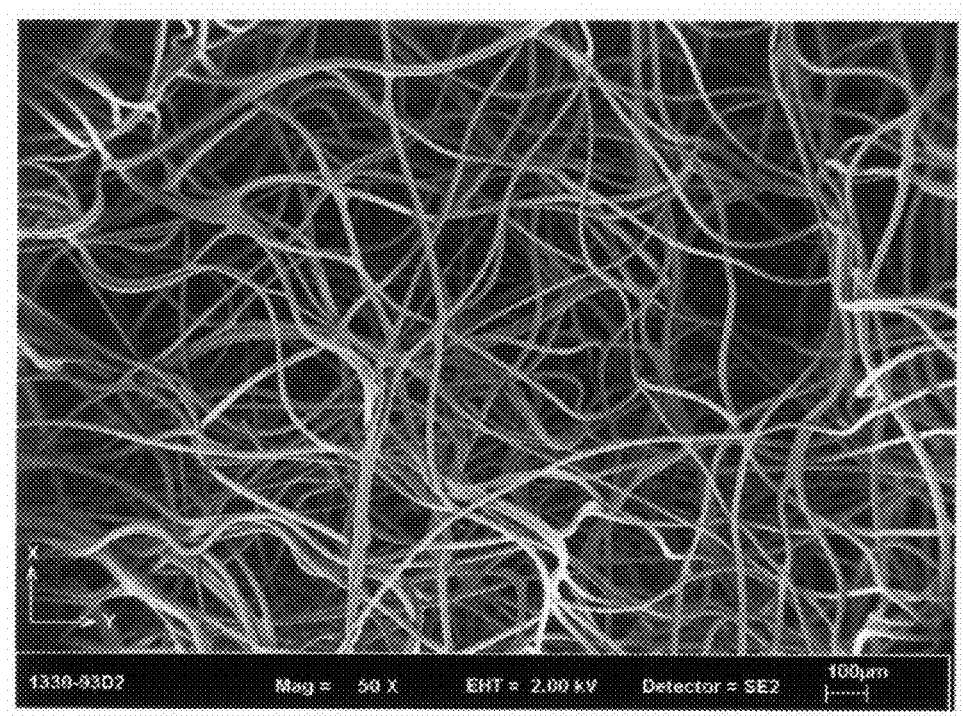
FIG. 4 is a scanning electron micrograph (SEM) of an embodiment of the present invention having a form referred to herein as fleece.
Figure 4A:
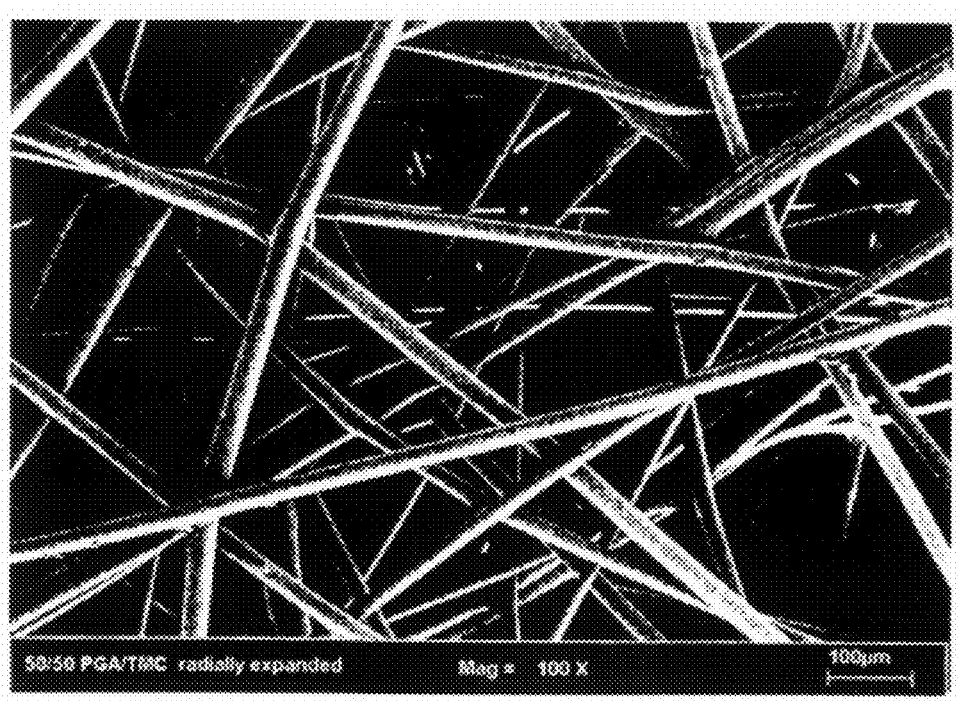
FIG. 4A is a scanning electron micrograph (SEM) of an embodiment of the present invention having been stretched in all directions outwardly from the center of the material.

Similar conditions are used for radially stretched precursor web materials (FIG. 4A). A radial stretch ratio of 3.75:1 (area ratio of 14:1) is preferred, although a stretch ration of 4.5:1 (area ratio of 20:1) works well. As in uniaxial and biaxial stretched webs, either annealing method described above may be employed.

Highly porous stretched self-cohered web materials of the present invention can be combined with one another to form layered or laminated materials. Optionally, the materials can be further processed with heat, binders, adhesives and/or solvents to attach the individual layers together. Alternatively, portions of one or more of the layers can remain unattached and separated to form a space between the layers.

Figure 13:
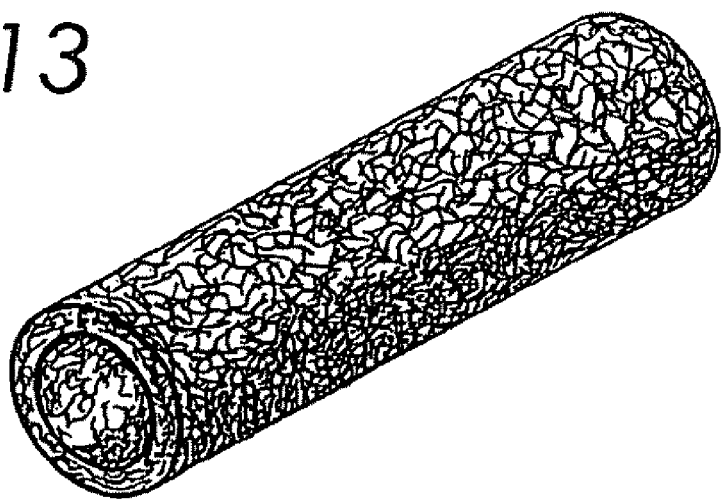
FIG. 13 is an illustration of a web material of the present invention having a tubular form.
Figure 17:
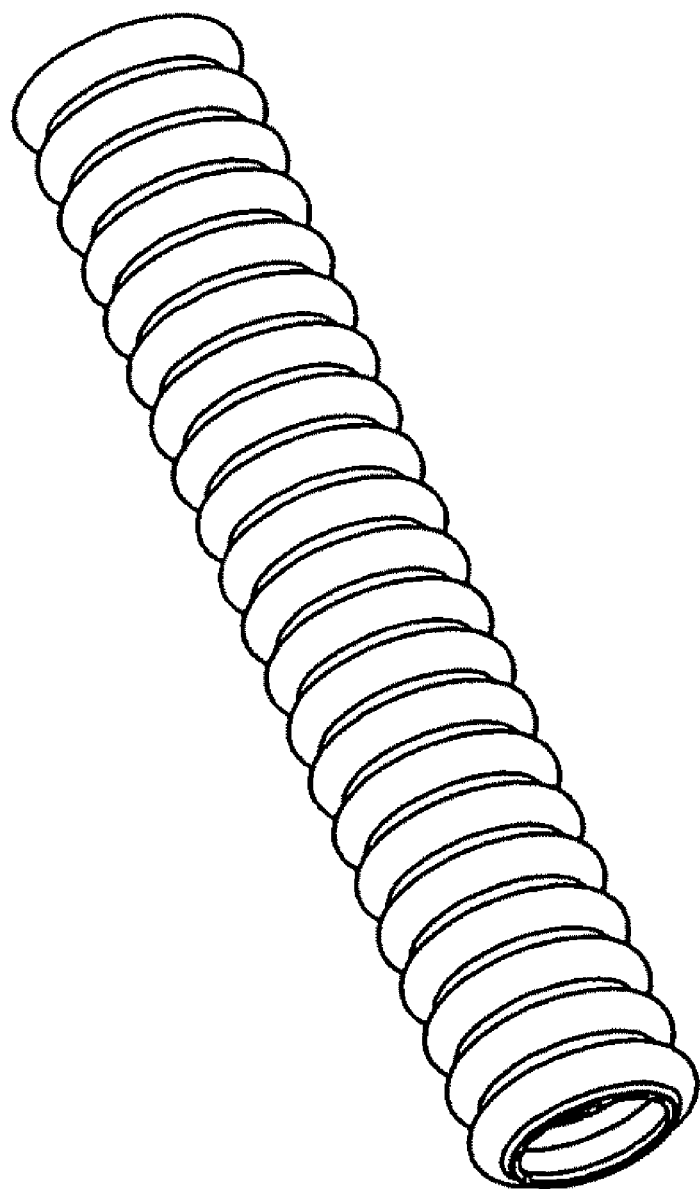
FIG. 17 is an illustration of a web material of the present invention in a tubular form having an ability to change dimension radially and longitudinally.

In some embodiments, highly porous stretched self-cohered web materials can be made in the form of a rod, cylinder (FIG. 14), rope, or tube (FIG. 13). The tubular form can be made in a "stretchy" form that can elongate and/or increase in diameter (FIG. 17). These and other forms can be adapted for use with a particular anatomical structure or surgical procedure. For example, a highly porous stretched self-cohered web material in the form of a sheet can be adapted for placement around an anastomotic junction and sutured or stapled in place (FIG. 11). In another embodiment (FIG. 10), a pledget material (14) is combined with a "stretchy" form of the present invention (12) to effect a substantially tubular structure (10) adapted to facilitate temporary placement of the pledget component onto a stapling apparatus cartridge (FIGS. 10A-10B). Alternatively, the present invention can additionally serve as the pledget component.

Figure 12:
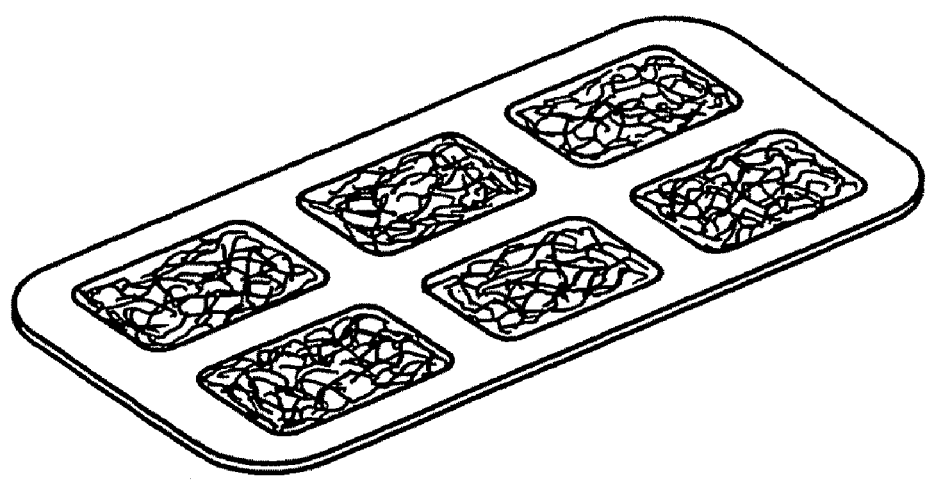
FIG. 12 is an illustration of a web material of the present invention placed between a second material having openings therein through which the web material is exposed.
Figure 15:
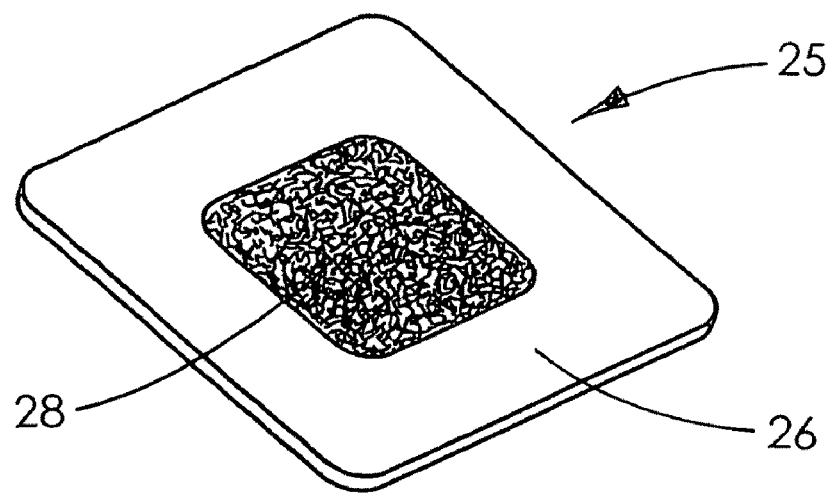
FIG. 15 is an illustration of a web material of the present invention and a non-bioabsorbable material.

In addition, a highly porous stretched self-cohered web material of the present invention can be combined with other materials to form composite devices (FIG. 15). In one embodiment, a sheet of stretched self-cohered bioabsorbable web material (28) is provided with a planar non-bioabsorbable material (26) surrounding the web material to form a dental implant (25). When implanted, bone or other tissue is encouraged to grow in a space defined by the implant. With time, the bioabsorbable web material is removed from the implantation site by natural physiological processes of the implant recipient while bone or other tissue ingrows and fills the space. Once the bioabsorbable portion of the implant has disappeared, another dental implant can be placed at the regenerated bone or tissue present at the site exposed by the bioabsorbed web material of the present invention. An alternative embodiment is illustrated in FIG. 12.

Figure 21:
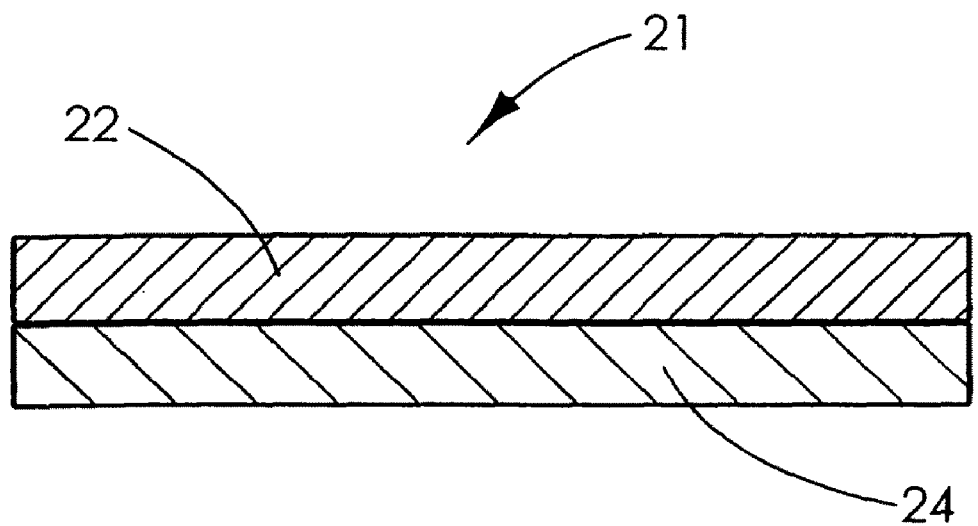
FIG. 21 is an illustration of a composite material having a stretched self-cohered web material layered on a non-bioabsorbable material.
Figure 21A:
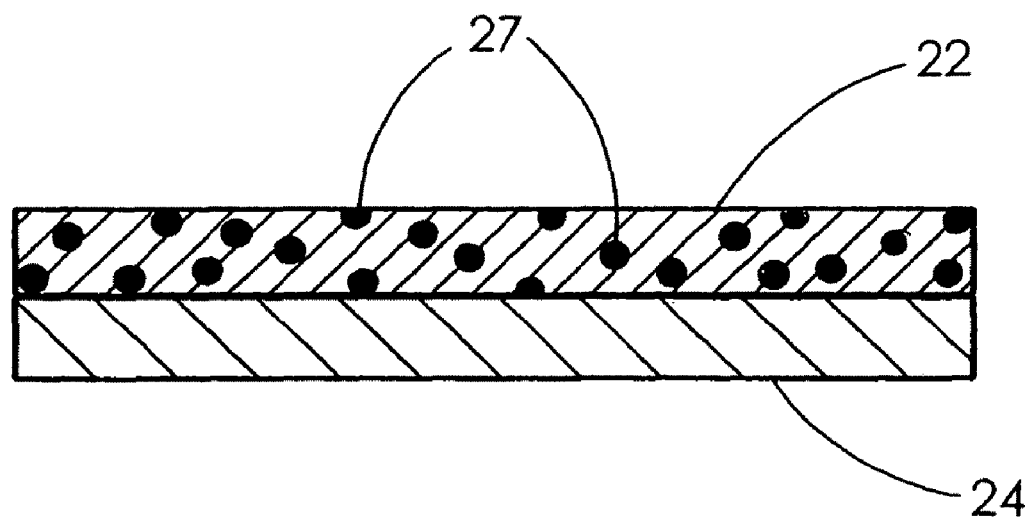
FIG. 21A is an illustration of a composite material having a stretched self-cohered web material having a bioactive species releasably contained therein layered on a non-bioabsorbable material.

In another embodiment, a highly porous stretched self-cohered web material (22) of the present invention is layered, and optionally laminated, to a sheet of non-bioabsorbable material (24). This composite material (21) is particularly suited for use as a dura substitute in cranial surgery (FIG. 21). Preferred non-bioabsorbable materials are fluoropolymeric in composition, with porous expanded polytetrafluoroethylene (ePTFE) and/or fluorinated ethylene propylene (FEP) being most preferred. Bioactive substances (27) can be placed in or on the highly porous stretched self-cohered web material of the present invention (FIG. 21A).

In other embodiments (FIG. 16), structural elements (39) are combined with a highly porous stretched self-cohered web material (38) to form a composite construction (36). The structural elements can be made of non-bioabsorbable and/or bioabsorbable materials. The structural elements can be placed on one or both sides of the stretched self-cohered web material. The structural elements can also be placed within the web material.

Figure 19:
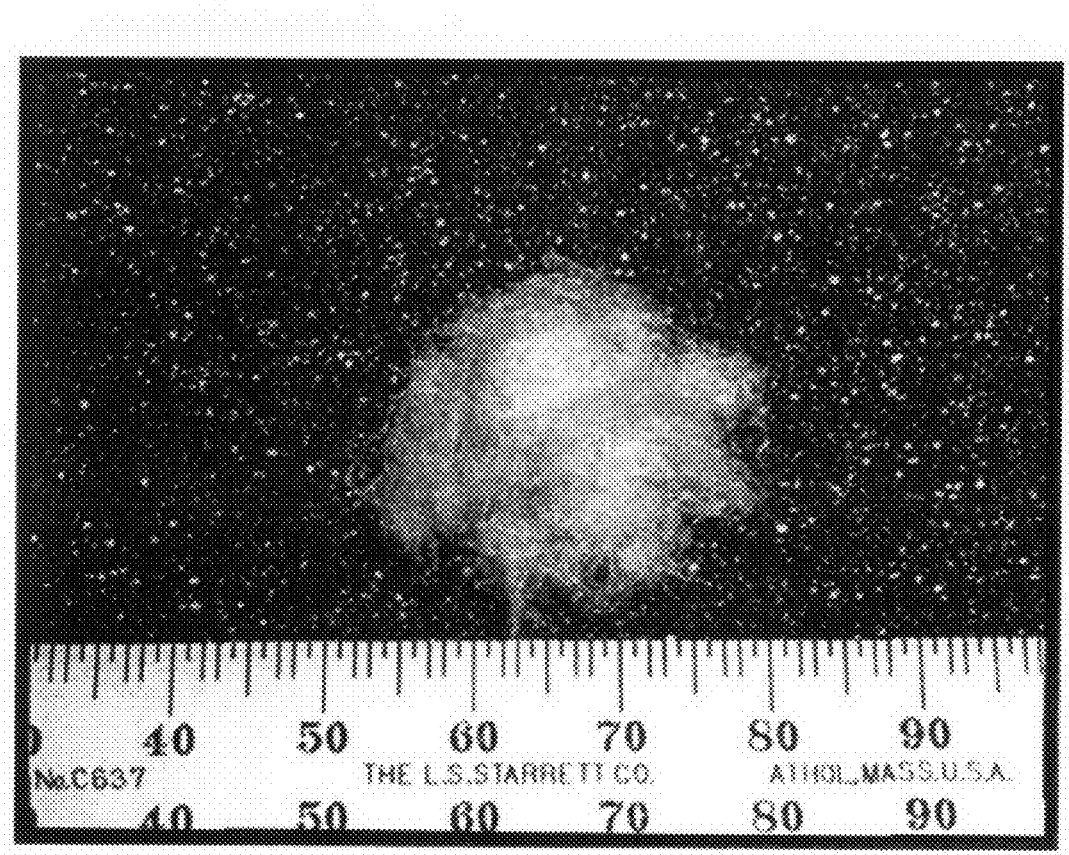
FIG. 19 is a photograph of a web material of the present invention having a very high degree of porosity.

The high porosity of stretched self-cohered web materials of the present invention can be increased further by subjecting the web material to a procedure that pulls the filaments apart to an even greater extent. The procedure may also fracture the continuous filaments of the stretched web material into pieces. These very porous stretched self-cohered web materials of the present invention have been shown to have highly thrombogenic properties. In a preferred form, the web material (49) has the appearance of a "cotton ball" (FIG. 19). One or more of these reversibly compressible "thrombogenic cotton balls" (49) can be combined with a delivery system (48), such as a catheter, for implantation at a site of bleeding or aneurysm formation (FIG. 20). Additional elements, such as metallic bands (FIGS. 19A-B), can be added to the very highly porous stretched self-cohered web material as visualization aids or mechanical supports. When used as a component for a medical device, these very highly porous, thrombogenic web materials can provide a seal between the device and surrounding anatomical structures and tissues.

Figure 9:
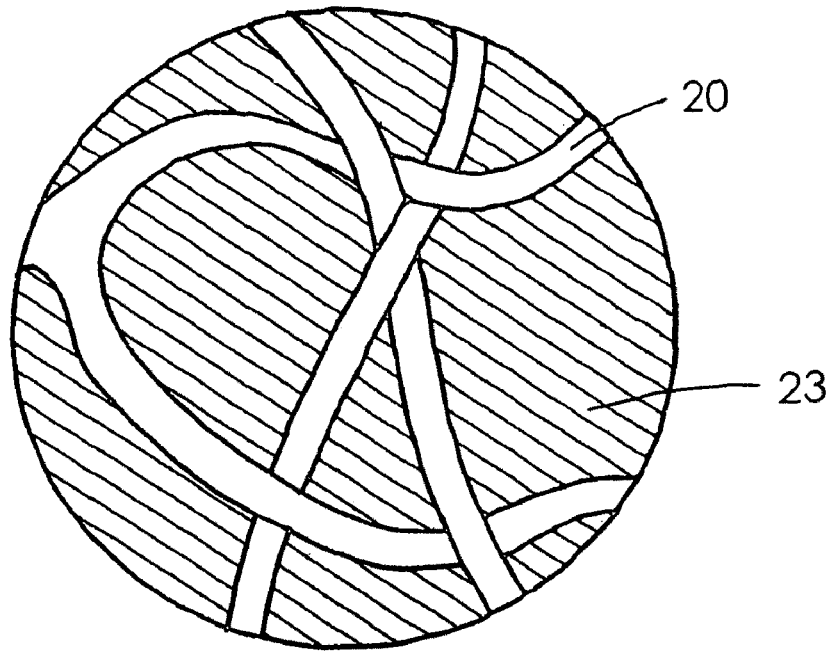
FIG. 9 in an illustration of a web material of the present invention having at least one additional material placed on surfaces and in void spaces of the web material.
Figure 9A:
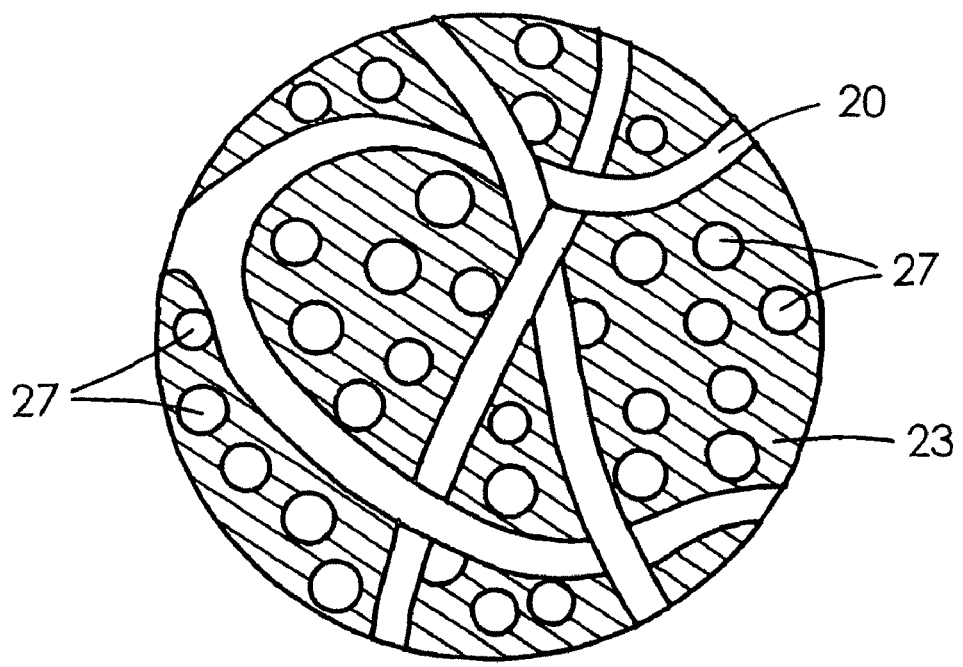
FIG. 9A is an illustration of a web material of the present invention having at least two additional materials placed on surfaces and in void spaces of the web material.

Various chemical components (23) can be combined with the highly porous web stretched self-cohered web materials (20) of the present invention (FIG. 9). The chemical components can be placed on surfaces of the polymeric material comprising the highly porous web material. The chemical components can also be placed in void spaces, or pores, of the web material. The chemical compositions can be suitably viscous chemical compositions, such as a hydrogel material. Biologically active substances (27) can be combined with the additional chemical component (FIG. 9A). With hydrogel materials, for example, the biologically active substances can be released directly from the hydrogel material or released as the hydrogel material and the underlying web material are bioabsorbed by the body of an implant recipient. Preferred chemical components are in the form of hydrogel materials.

Suitable hydrogel materials include, but are not limited to, polyvinyl alcohol, polyethylene glycol, polypropylene glycol, dextran, agarose, alginate, carboxymethylcellulose, hyaluronic acid, polyacrylamide, polyglycidol, poly(vinyl alcohol-co-ethylene), poly(ethyleneglycol-co-propyleneglycol), poly(vinyl acetate-co-vinyl alcohol), poly(tetrafluoroethylene-co-vinyl alcohol), poly(acrylonitrile-co-acrylamide), poly(acrylonitrile-co-acrylic acid-acrylamidine), poly(acrylonitrile-co-acrylic acid-co-acrylamidine), polyacrylic acid, poly-lysine, polyethyleneimine, polyvinyl pyrrolidone, polyhydroxyethylmethacrylate, polysulfone, mercaptosilane, aminosilane, hydroxylsilane, polyallylamine, polyaminoethylmethacrylate, polyomithine, polyaminoacrylamide, polyacrolein, acryloxysuccinimide, or their copolymers, either alone or in combination. Suitable solvents for dissolving the hydrophilic polymers include, but are not limited to, water, alcohols, dioxane, dimethylformamide, tetrahydrofuran, and acetonitrile, etc.

Optionally, the compositions can be chemically altered after being combined with the web material. These chemical alterations can be chemically reactive groups that interact with polymeric constituents of the web material or with chemically reactive groups on the compositions themselves. The chemical alterations to these compositions can serve as attachment sites for chemically bonding yet other chemical compositions, such as biologically active substances (27). These "bioactive substances" include enzymes, organic catalysts, ribozymes, organometallics, proteins, glycoproteins, peptides, polyamino acids, antibodies, nucleic acids, steroidal molecules, antibiotics, antimycotics, cytokines, carbohydrates, oleophobics, lipids, extracellular matrix material and/or its individual components, pharmaceuticals, and therapeutics. A preferred chemically-based bioactive substance is dexamethasone. Cells, such as, mammalian cells, reptilian cells, amphibian cells, avian cells, insect cells, planktonic cells, cells from non-mammalian marine vertebrates and invertebrates, plant cells, microbial cells, protists, genetically engineered cells, and organelles, such as mitochondria, are also bioactive substances. In addition, non-cellular biological entities, such as viruses, virenos, and prions are considered bioactive substances.

The following examples are included for purposes of illustrating certain aspects of the present invention and should not be construed as limiting.

EXAMPLES

Example 1

This example describes formation of an article of the present invention. Initially, an unannealed, non-woven, self-cohered polymeric precursor web was formed. The precursor web material was heated slightly and subjected to stretching in a single, or uniaxial, direction to increase the porosity of the web material. The highly porous self-cohered web material was then set with heat.

The precursor web material was formed from a 67% poly(glycolide) and 33% poly(trimethylenecarbonate) (w/w) segmented triblock copolymer (67% PGA:33% TMC). The copolymer is available in resin form from United States Surgical (Norwalk, Conn., US), a unit of Tyco Healthcare Group LP. This polymer is commonly referred to as polyglyconate and has historically been available through the former Davis & Geck (Danbury, Conn.). A typical 67% PGA:33% TMC resin lot was characterized previously by Hayes in U.S. Pat. No. 6,165,217, which is incorporated herein by reference. The process of characterizing the "67:33-PGA:TMC" resin material is reiterated herein.

Approximately 25 mg of the acquired copolymer was dissolved in 25 ml of hexafluoroisopropanol (HFIP). The dilute solution thus produced had an inherent viscosity (IV) of 1.53 dl/g as measured with a Cannon-Ubelodde viscometer immersed in a water bath set at 30° C. (+/−0.05° C.).

Approximately 10 mg of the acquired copolymer was placed into an aluminum differential scanning calorimetry (DSC) sample pan, covered, and analyzed utilizing a Perkin-Elmer DSC 7 equipped with an Intracooler II cooling unit able to provide sample cooling to temperatures as low as minus forty degrees centigrade (−40° C.). After preconditioning of the sample at 180° C. for 2 minutes, the sample was cooled at the maximum rate provided by the instrument (−500° C./min setting) and scanned from minus forty degrees centigrade (−40° C.) to two hundred fifty degree centigrade (250° C.) at a scanning rate of 10° C./min. After completion of this initial scan, the sample was immediately cooled at the maximum rate provided by the instrument (−500° C./min setting). A second similar scan was undertaken on the same sample over the same temperature range. After scan completion and thermal maintenance at 250° C. for 5 minutes, the sample was again cooled at the maximum rate provided by the instrument and a third scan undertaken.

Each scan was analyzed for the observed glass transition temperature ($T_g$), order-disorder transition temperature ($T_{odt}$), crystallization exotherm, and melt endotherm. The results are summarized in Table 1.

TABLE 1

|  | $T_g/T_{odt}$ | $T_g/T_{odt}$ | Exotherm Peak | Exotherm Enthalpy | Melt Peak | Melt Enthalpy |
|---|---|---|---|---|---|---|
| Heat 1 | 0.2° C. | 0.26 J/g * ° C. | None | None | 213.7° C. | 44.7 J/g |
| Heat 2 | 17.0° C. | 0.59 J/g * ° C. | 113.7° C. | −34.2 J/g | 211.4° C. | 41.2 J/g |
| Heat 3 | 17.0° C. | 0.51 J/g * ° C. | 121.4° C. | −35.3 J/g | 204.2° C. | 38.5 J/g |

To prepare the copolymeric resin for processing into a precursor web material, approximately 100 grams of the copolymer was heated overnight under vacuum (<40 mm Hg) between 115° C. and 135° C. The resin was pelletized by grinding the copolymer through a granulator equipped with a screen having four (4) mm holes (Model 611-SR, Rapid Granulator, Rockford, Ill., USA).

A one-half inch screw extruder (Model RCP-0500, Randcastle Extrusion Systems, Inc., Cedar Grove, N.J., USA) with an attached fiber spin pack assembly (J. J. Jenkins, Inc., Matthews, N.C., USA) was obtained. The bottom portion of the spin pack assembly had a seven (7) orifice spinnerette (see "Spin Pack" in FIG. 5) consisting of 0.33 mm (0.013 inches) diameter die openings arranged in a 2.06 cm (0.812 inches) diameter circular configuration. The spin pack was set to a temperature of between 250° C. and 270° C. The particular temperature was dependent on inherent viscosity characteristics of the resin.

Figure 5:
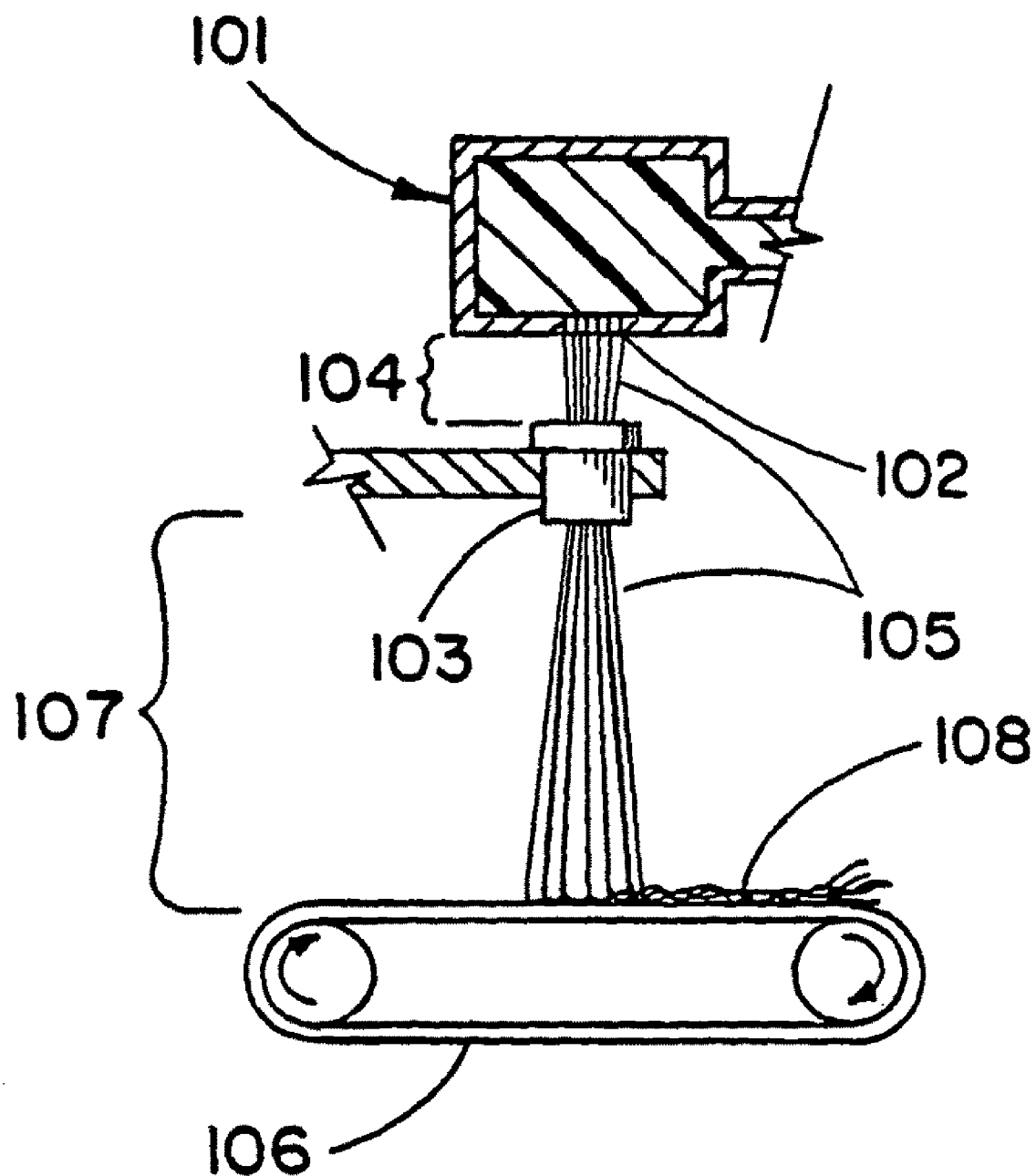
FIG. 5 is a schematic illustration of an apparatus suitable to produce a precursor web material for use in the present invention.

An adjustable arm holding a Vortec Model 902 TRANSVECTOR® (Vortec Corporation—Cincinnati, Ohio USA) was attached to the spin pack and positioned in alignment with the travel direction of a screen fabric collector belt and below the base of the spinnerette (FIG. 5). The top of the TRANSVECTOR® inlet was centered below the die openings at an adjusted distance "A" (FIG. 5) of approximately 2.5 to 3.8 cm (1.0 to 1.5 inches). The arm was mounted on a mechanical apparatus that caused the TRANSVECTOR® to oscillate across the fabric collector in the same direction as a moving take-up belt. The arm oscillated between angles approximately five (5) degrees off center at a frequency of rate of approximately 0.58 full sweep cycles per second (approximately 35 full cycles per minute). The TRANSVECTOR® was connected to a pressurized air source of approximately 50 to 55 psi (0.34-0.38 MPa). The pressurized air was at room temperature (20-25° C.), a temperature in excess of the polymer's $T_{odt}$. When operating, the pressurized air was introduced and accelerated within the TRANSVECTOR®'s throat. The accelerated air stream drew additional air into the inlet from the area of the multiple orifice die.

The vacuum dried pelletized copolymer was then fed into the screw extruder (101) and through the crosshead of the spinneret (102) as illustrated in FIG. 5. The melted copolymer exited the spinnerette in the form of seven (7) individual filaments (105). As the filaments became influenced by the air current entering the TRANSVECTOR® inlet (103), the filaments were accelerated through the TRANSVECTOR® at a significantly higher velocity than without the air entrainment. The accelerated filaments were then accumulated on a screen fabric collector belt (106) located at a distance "107" 66 cm (26 inches) from the outlet of the TRANSVECTOR® and moving at the speed of approximately 20.4 cm/min (0.67 feet per minute) to form a precursor web material (108). Increasing the belt speed produced a thinner web material, while slowing the belt speed produced a thicker web material.

The resulting unannealed, unstretched, non-woven, filamentous, self-cohered precursor web material that accumulated on the collector belt possessed a relatively consistent loft along the direction of belt movement and possessed approximately 3.2 inches of "usable width." "Usable width" refers to an inner portion of the precursor web material having the greatest consistency at a gross, visual level, and a fine, microscopic, level. Portions of precursor web material outside the "usable width" have filaments that accumulate in such a way that the overall web diminishes in relative height and density on either side of the centerline when observed in line with the direction of belt movement. Area densities reported herein were obtained from representative samples acquired from a region of the web having a "usable width."

After more than 10 seconds of cooling at ambient temperature, the precursor web was removed from the fabric belt. Upon examination, the material was a tactilely supple, cohesive fibrous web, with individual component fibers that did not appear to fray or separate from the web when subjected to moderate handling. The filaments were intermingled and bonded at contact points to form an un-annealed (i.e. minimally crystallized or "unset"), unstretched, non-woven, self-cohered precursor web material.

Precursor webs produced in this manner typically possess inherent viscosity (IV) values and crystallization exotherm peaks similar to those described in Example 2 of U.S. Pat. No. 6,165,217, issued to Hayes, and incorporated herein by reference. Particularly pertinent portions of the example are reproduced herein as follows.

Inherent Viscosity

Approximately 29 mg of the above-described precursor web was dissolved in 25 ml of hexafluoroisopropanol (HFIP) to produce a dilute solution. The solution possessed an inherent viscosity (IV) of 0.97 dl/g when measured using a Canon-Ubbelohde viscometer immersed in a 30° C. (+/−0.05° C.) water bath. Consequently, the IV was observed to have dropped during processing from the initial value of 1.53 dl/g in the pelletized copolymer to a value of 0.97 dl/g in the precursor web.

Thermal Properties

An appropriately sized sample was obtained from the above-described precursor web to allow for its thermal analysis utilizing a Perkin Elmer DSC7 Differential Scanning Calorimeter (DSC). Scanning was conducted at 10°

C./minute and the instrument's temperature was moderated with an Intracooler II refrigeration unit. A single scan between minus twenty degrees centigrade (−20° C.) and 250° C. was performed with the following results (TABLE 2).

TABLE 2

| | $T_g/T_{odt}$ | $T_g/T_{odt}$ Capacity | Exotherm Peak | Exotherm Enthalpy | Melt Peak | Melt Enthalpy |
|---|---|---|---|---|---|---|
| Heat 1 | 16.32° C. | 0.54 J/g * ° C. | 88.16° C. | −31.68 J/g | 209.70° C. | 45.49 J/g |

The order-disorder transition temperature ($T_{odt}$) reported herein occurs at the inflection point between the differing levels of heat capacity as indicated by a deflection of greater than 0.1 joule per gram-degree Celsius (J/g*° C.) in the baseline of the scan. This $T_{odt}$ occurs at a temperature between the glass transition temperatures ($T_g$) of the respective homopolymers and is roughly approximated by the Fox equation. In this particular example, the precursor web sample displayed an order-disorder transition at approximately 16° C. and a crystallization exotherm beginning at approximately 70° C. Full specimen crystallinity is considered proportional to the area under the melt endotherm, quantified by enthalpy in Joules/gram (J/g). The general characteristics of a thermal scan of this precursor web can be observed in FIG. 3 of the above-referenced '217 patent.

Assuring that the web was not exposed to combinations of heat or time that would lead to a substantial reduction of the precursor web's crystallization exotherm enthalpy, as measured through the aforementioned evaluation with a power compensation based DSC system, opposite ends of rectangular segments of the precursor web were then placed under restraint and stretched in a single, or uniaxial, transverse direction (i.e., in a direction approximately 90 degrees from the longer length of the precursor web).

The highly porous stretched self-cohered web materials of the present invention were made with a transverse expansion/stretching machine equipped with pin grips and three electric heating zones. Such a machine is also known as an adjustable tenter or stenter frame with the capability to expand transversely across the surface of a supporting metal sheet while moving in a longitudinal direction. Due to broad adjustability, various machines able to fulfill the functions described herein are available from numerous suppliers, one of which is: Monforts, A Textilmaschinen GmbH & Co KG, Moechengladbach, Germany.

This particular unit was equipped with three (3) sequential conjunct heated platens measuring 24, 6, and 24 inches (61, 15.2, and 61 cm) in length, respectively. The heated platens created heated zones through which the web material was passed. The leading edge of a 13 inch (33 cm) long stretching-transition region began 11 inches (27.9 cm) from the leading edge of the first heated zone. The initial feed rate was one (1) foot (30.48 cm) per minute.

In the initial stretching operation, only the third, or last downstream, zone of the stretching machine was heated to a temperature of 120° C. However, it was serendipitously discovered that heat from the third zone progressively invaded the adjoining second and first zones in such a way that the precursor web was warmed before it was stretched. Inter alia, this resulted in progressively improving uniformity of the final highly porous web material. Precursor web materials were stretched at ratios of 2:1, 3:1, 4:1, 5:1 and 6:1. Preferred materials were formed when zone one (1) of the transverse stretching apparatus was set at a temperature of 50° C. and the precursor web material stretched at a ratio of 6:1.

After thermosetting the stretched web at a temperature of about 120° C. for about one (1) minute, a highly porous self-cohered web material of the present invention was formed and allowed to cool to room temperature. Each piece of inventive material was found to be more porous, supple, lofty, compliant, and uniform in appearance than a similar non-woven self-cohering web made without pre-heating and stretching of the similar web in an un-annealed state.

Additional rectangular sections of precursor web materials were stretched at ratios of 8:1 and 10:1 using preheated platens set to approximately 50° C., 75° C., and 125° C. for each successive heated zone in the stretching apparatus. The first two heat zone settings provided a reliable "pre-warming" of the precursor web material. The temperatures, in excess of the $T_{odt}$ reported in the '217 patent, were sufficient to facilitate mobility of the co-polymeric molecules of the precursor web material and provide a more consistent final product. The third heated zone was set to a temperature that at least approximated and likely exceeded the temperature of the crystallization Exotherm Peak ($T_{cr}$) described within the '217 patent, to anneal, or heat-set, the final web material.

Example 2

In this example, precursor webs produced using the various belt speeds and transverse expansion ratios described in Example 1 were obtained for a variety of web densities and stretch, or draw, ratios. Following processing, scanning electron micrographs (SEM) were generated of representative areas of this embodiment of the present invention. Some characteristics of the stretched web of the present invention and the filaments comprising the web were quantified as follows.

Figure 6:
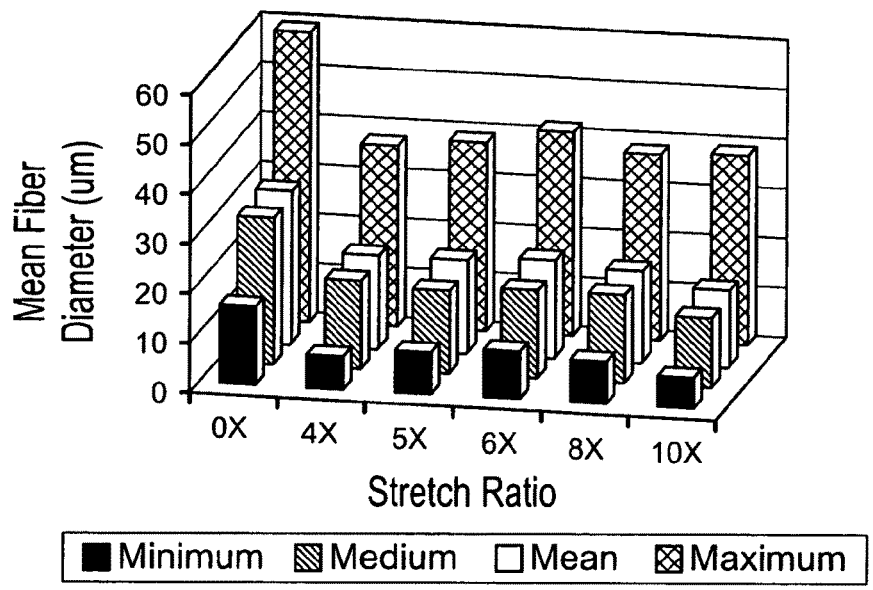
FIG. 6 is a graph showing the effect of different stretching ratios on the diameter of the filaments in the finish web material of the present invention.
Figure 7:
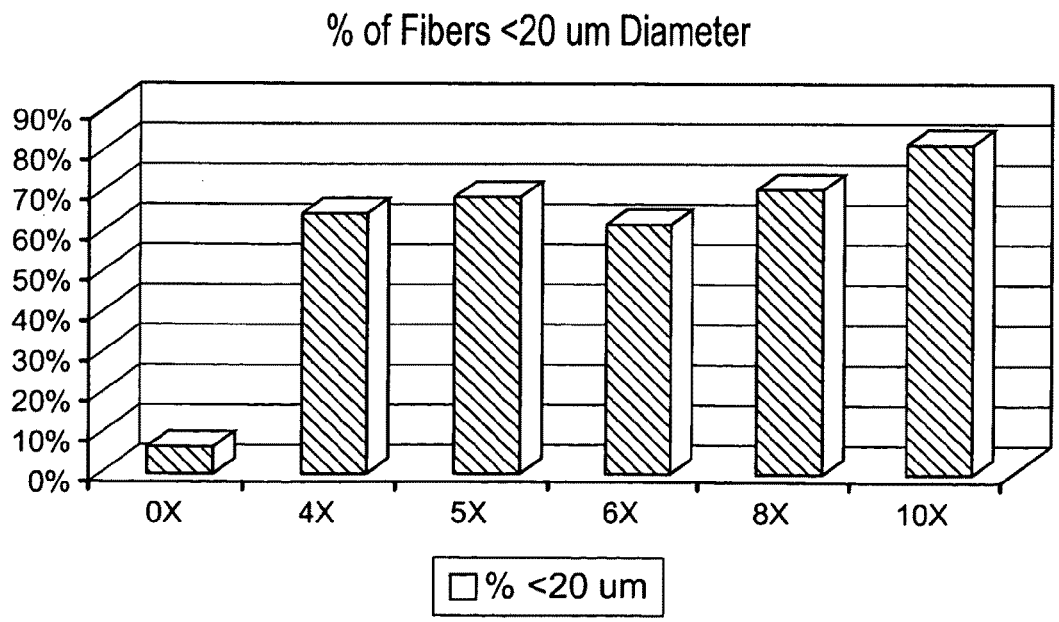
FIG. 7 is a graph showing the percentage of filaments having a diameter less than twenty (20) microns for a given stretching ratio.

The cross-sectional diameter of the stretched filaments in each web material of the present invention was determined by visually examining the SEMs. In each SEM, fifty (50) stretched filaments were randomly chosen and the diameter of a cross-section of each filament was measured. The cumulative results of these filament cross-sectional diameters is contained in Table 3 and summarized in FIGS. 6 and 7. The stretch ratios are expressed as multiples of "X." For example, "0X" refers to unstretched precursor web material. "4X" refers to a 4:1 stretch ratio. Tabulated features of the web were the mean, median, maximum, and minimum fiber diameter. In addition, both the number and percent of the fifty (50) fibers found to be less than twenty (20) microns in cross-sectional diameter were tabulated.

TABLE 3

Fiber Dimensional Characteristics at Varying Stretch Ratios

| | 0X | 4X | 5X | 6X | 8X | 10X |
|---|---|---|---|---|---|---|
| Mean | 31.3 | 19.3 | 19.2 | 20.2 | 19.0 | 16.0 |
| Median | 30.3 | 18.6 | 17.6 | 18.4 | 18.6 | 15.0 |
| Web Sample Count | 6 | 2 | 2 | 10 | 2 | 2 |
| Fiber Count (<20 um) | 2.8 | 32.0 | 34.0 | 30.5 | 35.0 | 40.5 |

TABLE 3-continued

Fiber Dimensional Characteristics at Varying Stretch Ratios

|  | 0X | 4X | 5X | 6X | 8X | 10X |
|---|---|---|---|---|---|---|
| % < 20 um | 5.7% | 64.0% | 68.0% | 61.0% | 70.0% | 81.0% |
| % > 20 um | 94.3% | 36.0% | 32.0% | 39.0% | 30.0% | 19.0% |
| % > 50 um | 1.3% | 0.0% | 0.0% | 0.6% | 0.0% | 0.0% |
| Minimum (um) | 17.0 | 7.6 | 9.6 | 10.6 | 9.7 | 7.3 |
| Maximum (um) | 59.4 | 37.3 | 38.9 | 41.9 | 38.2 | 39.1 |

When evaluated with this method, all the fiber cross-sectional diameters in the unannealed, unstretched, precursor web (0X) were observed to be between seventeen (17) and fifty-nine (59) microns. Further, over ninety percent (90%) of the fibers had cross-sectional diameters within the twenty (20) and fifty (50) micron range described in the above-referenced '217 patent. The effect of stretching on the fiber diameter is readily seen from this data. Filaments of unstretched precursor webs can be reduced in diameter when subjected to the stretching process of the present invention. The reduction in fiber diameter is readily seen by contrasting the number of fibers in an unstretched web having diameters below twenty (20) microns (e.g., 5.7%) with the number of fibers of stretched webs having diameters below twenty (20) microns. The number of fibers with diameters less than twenty (20) microns in a stretched material of the present invention range from an average of sixty four percent (64%) to eighty one percent (81%). Accordingly, substantial stretching of a precursor web causes a significant reduction in fiber diameter in a substantial number of the fibers in the final stretched web material of the present invention.

Since these webs were stretched, or drawn, in a single direction, or "uniaxial" manner, it is notable from this same data that twenty (20) to forty (40) percent of the fibers in the stretched web have diameters larger than 20 microns. This mix of fiber diameters within the stretched web resulted in an increase in the web material's overall loft. The Increased the loft of the stretched web material correlates with a reduction in both the web's area density and the volume density. Volume density is directly related to porosity. Web materials of the present invention have increased porosity-compared to similar unstretched web materials. Increasing porosity and correspondingly reducing volume density maximizes interstitial space within the web structure. These features increase the opportunity for infiltration of host cells into the web material. The number and type of cell inhabiting a web material of the present invention have a direct effect on the bioabsorption of the web material.

To quantify the actual molecular orientation imparted by the stretching process of the present invention, birefringence values were determined for a variety of filaments from webs of the present invention made with different stretch ratios. Birefringence values were obtained by utilizing a sliding quartz wedge capable polarizing microscope possessing both an optical grid and a circular rotating stage (e.g. Nikon Optiphot2-POL). Both filament cross-sectional diameter and birefringence values were determined from a sampling of filaments that were either actively or passively isolated from the optical influences of the surrounding web.

Assuring no physical distortion artifacts occurred during filament isolation, cross-sectional diameter values were determined using convention light microscopy and birefringence values. The values were acquired through utilization of a Michel-Levy chart. Such optical equipment is available from various suppliers (e.g., Nikon America, Melville, N.Y.). Michel-Levy charts are also available from various suppliers (e.g., The McCrone Institute (Chicago, Ill.).

Figure 8:
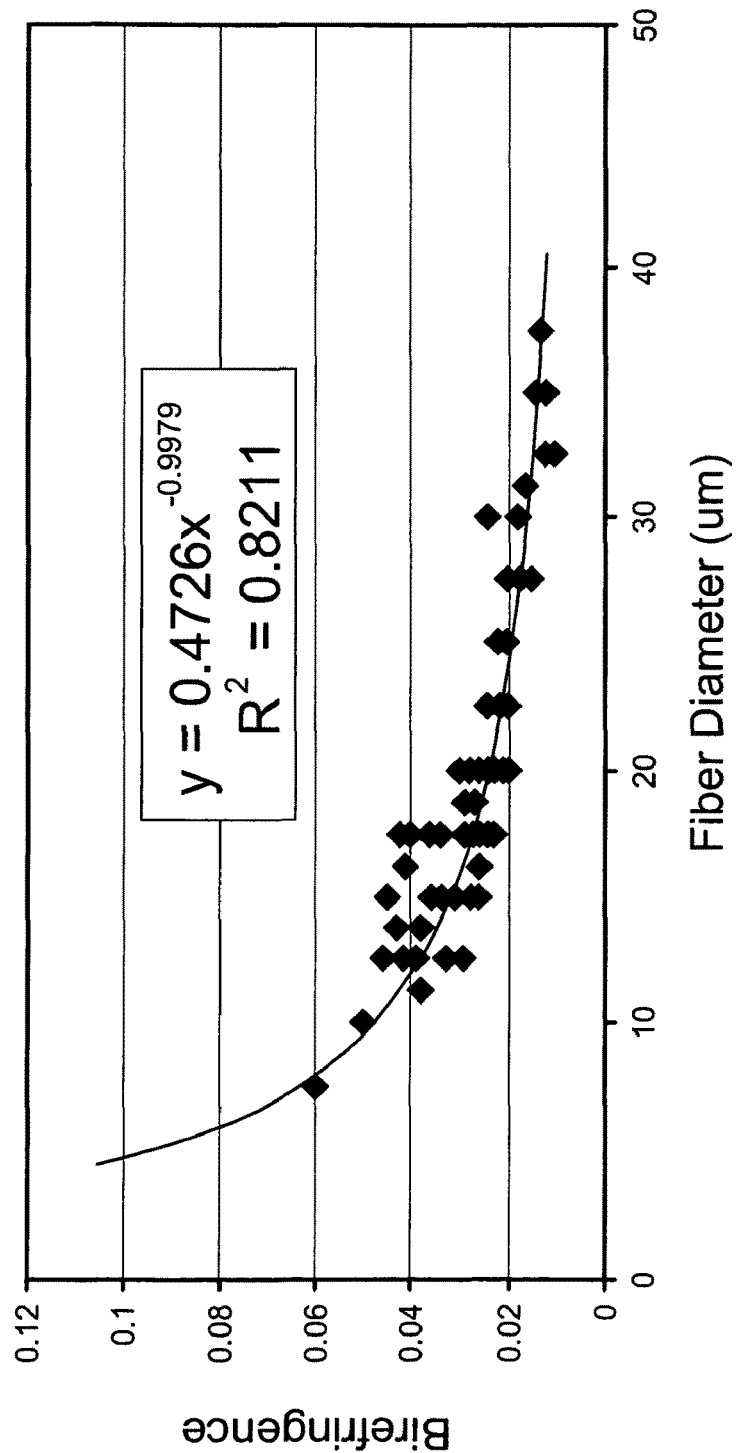
FIG. 8 is a graph showing the relationship of birefringence to filament diameter in a finished web material of the present invention.

The birefringence values thus obtained were analyzed for a correlation with filament diameter. It was found the relationship appeared to follow a power function that could be approximated by the equation:

$$Y = 0.4726 X^{-0.9979}$$

with an R2 value of 0.8211 (see FIG. 8). Using this relationship and referring to FIG. 8, it was determined that a filament with a twenty (20) micron cross-sectional diameter could be expected to possess a birefringence value of approximately 0.024. Thus, filaments having cross-sectional diameters less than twenty (20) microns could be reasonably expected to possess birefringence values in excess of 0.025.

Example 3

As a result of stretching the material described in Example 1, both the amount of polymeric material per unit area (area density) and amount of polymeric material per unit volume (volume density) were reduced. A precursor web (produced at a belt speed of 0.67 feet/minute (20.4 cm/minute)) was further processed in an oven set at 100° C. for 25 minutes to completely anneal, or "heat-set," the web material.

The unannealed, unstretched, self-cohered precursor web material was substantially similar to the web material disclosed in the '217 patent. A heat-set version of the precursor web material was determined to have an area density of approximate 23 mg/cm$^2$ and a volume density of approximately 0.16 g/cc. Commercially forms of this type of web are available from W.L. Gore & Associates, Inc., Flagstaff, Ariz., under the tradenames GORE Bioabsorbable SeamGuard and GORE Resolut Adapt LT. Each of these unstretched web materials has an area density of 9.7 mg/cm$^2$ and 8.4 mg/cm$^2$, respectively. Each web material also had a volume density of 0.57 g/cc and 0.74 g/cc, respectively. This corresponded to a percent porosity of fifty-six (56) and forty-three (43), respectively.

After uniaxial stretching of a precursor web material of Example 1 at a ratio of 6:1, the material was determined to have an area density of approximately 5.3 mg/cm$^2$. This represents a change in area density of approximately seventy-five percent (75%). The unstretched precursor web material of Example 1 had a volume density of 0.16 g/cc. In contrast, the stretched web material of Example 1 had a volume density of 0.083 g/cc. This represents a reduction in volume density of approximately fifty (50) percent.

The specific gravity of full density, unstretched, 67% PGA: 33% TMC (w/w) polymer ($\rho_{polymer}$) has been reported to be 1.30 grams/cc (Mukherjee, D, et al; Evaluation Of A Bioabsorbable PGA: TMC Scaffold For Growth Of Chondrocytes, Abstract #12, Proceedings of the Society for Biomaterials, May 2005). By comparing this reported polymeric density value with the volume density of a web material of the present invention ($\rho_{scaffold}$), overall percentage porosity in the absence of additional components can be determined through the relationship:

$$(\rho_{polymer} - \rho_{scaffold}) \div \rho_{polymer} \times 100$$

As used herein, the term "percent porosity" or simply "porosity" is defined as the void space provided within the external boundaries of the stretched self-cohering web, absent the inclusion of any fillers or other added components that may effectively reduce the available porosity.

This evaluation showed that stretching the precursor web material of Example 1 increased the percent porosity of the PGA:TMC precursor web material from eighty-eight percent (88%) in the absence of additional components to approximately ninety-four percent (94%) in the absence of additional components. The resulting percent porosity in the absence of additional components of both the precursor and aforementioned 6:1 stretched web is provided in Table 4. Table 4 also provides a summary of the area density, the volume density, and the percent porosity of the web material before and after stretching.

TABLE 4

Physical Property Comparison of 6:1 Stretched Web

| Observation | Precursor Web @ 0.67 feet/minute | 6:1 Stretched Web | Percent (%) Change |
|---|---|---|---|
| Density PGA:TMC = 1.30 g/cc | | | |
| Area Density (in mg/cm$^2$) | 23 | 5.3 | −77% |
| Volume Density (in g/cm$^3$) | 0.158 | 0.083 | −47% |
| Percent Porosity in the absence of additional components | 88% | 94% | 7% |

Example 4

This example describes generation of tensile stress-strain data for uniaxially stretched (6:1 stretch ratio) web materials of the present invention. The web materials were produced according to Example 1 with the exception that the belt speed was 0.26 feet/minute (7.9 cm/sec).

Samples of stretched web materials of the present invention were cut into shapes having a central strip and enlarged ends, much like that of a "dog bone." The dog bone-shaped specimens were approximately half the size of those described for ASTM D638 Type IV (i.e., with a narrow distance length of 18 mm and a narrow width of 3 mm). Testing was conducted using an INSTRON® Tensile Tester Model No. 5564 equipped with an extensometer and 500 Newton load cell. The software package used to operate the tester was Merlin, Version 4.42 (Instron Corporation, Norwood, Mass.). The gauge length was 15.0 mm. The cross-head rate (XHR) was 250 mm/minute. Data was acquired every 0.1 second.

The percentage (%) elongation and matrix tensile stress of the stretched web, as measured from test specimens oriented in their length to be in line with in the stronger cross-web direction, was found to be 32.0% and 60 MPa, respectively. The percentage (%) elongation and matrix tensile stress of the stretched web, as measured from test specimens oriented in their length as measured in the weaker down-web direction, was found to be 84.7% and 3.4 MPa, respectively. Tensile stress results for these 67:33-PGA:TMC webs are summarized in Table 5 For comparative purposes, the mechanical characterization of a thinner web of 67:33-PGA:TMC as described in the '217 patent is included in Table 5.

Matrix tensile stress is utilized as a means to normalize tensile stress in samples where measurement of thickness can be problematic, such as materials of the present invention possessing a high degree of porosity and easily deformed loft. Through utilization of the test material's area density and the specific gravity of its component polymer, the matrix tensile stress approach converts a difficult to measure porous loft into an equivalent thickness of full density component polymer. The reduction is proportional to the volume density of the web divided by the specific gravity of the component polymer. This equivalent polymeric thickness was then utilized for cross-sectional area determinations in the calculation of tensile stress. Such use of matrix tensile stress has been described in both U.S. Pat. No. 3,953,566, issued to Gore, and U.S. Pat. No. 4,482,516, issued to Bowman, et al. for utilization in determining the strength of porous expanded polytetrafluoroethylene (ePTFE) materials.

To obtain matrix tensile strength, the equivalent thickness of a tensile specimen is determined by dividing the porous structure's area density by the specific gravity of the component polymer. This value is then substituted instead of the specimen's actual thickness in determining stress. Thus:

Equivalent thickness=area density/specific gravity of polymer

Provided both the area density and the specific gravity of the component polymer are known, this equivalent thickness value can also be utilized to convert the tensile stress of a porous sample into a matrix tensile stress value. In Example 2 of the '217 patent, both maximum tensile stress of the 67:33-PGA:TMC web material was reported along with the area density of the test specimen and were found to be 4.9 MPa and 28.1 mg/mm$^2$, respectively.

Thus, matrix tensile stress can be calculated as follows:

TABLE 5

$$\frac{4.9 \text{ N}}{\text{mm}^2} \times \frac{\text{mm}^2}{[(28.1 \text{ mg}/100 \text{ mm}^2)/1.3 \text{ mg}/\text{mm}^3] \times 1 \text{ mm}} = 22.7 \text{ MPa}$$

| | Tensile | | | | Density | |
|---|---|---|---|---|---|---|
| Sample Description | Max Force (N) | Max Stress (MPa) | Matrix Stress (MPa) | % Elongation | Area (mg/cm$^2$) | Volume (g/cm$^3$) |
| Unstretched Precursor Web | n.a. | n.a. | n.a. | n.a. | 44 | .17 |
| U.S. Pat. No. 6,165,217 (Example 2; orientation not specified) | Not provided | 4.9 (saline) | 22.7 (calc'd) | Not provided | 28.1 | 0.29 |
| 6:1 Transverse Stretched Cross-Web Sample | 14.3 | 3.6 | 60 | 32.0 | 9.6 | .065 |
| 6:1 Transverse Stretched Down-Web Sample | 1.0 | 0.34 | 3.4 | 84.7 | 11.5 | .078 | na. = not acquired

As can be seen for the data, the web material of the present invention was found to be highly anisotropic and possessed reduced strength and significant elongation in the "down web" direction. Conversely, the strength was highest in the direction of stretching and cross-web matrix tensile stress was found to be significantly higher than the fully crystallized unstretched web material described in the '217 patent. This result provided evidence of increased molecular orientation of the PGA:TMC block copolymers.

Example 5

This example describes the formation of an article of the present invention using an ABA triblock copolymer of PGA:TMC having a ratio of poly(glycolide) to poly(trimethylenecarbonate) (w/w) of 50:50.

Synthesis of a typical 50% PGA:50% TMC resin lot has been previously described in the '217 patent and is reiterated herein as follows.

A 4CV Helicone Mixer (Design Integrated Technologies, Warrenton, Va., USA) located within a Class 10,000 clean room and connected to a Sterling brand hot oil system (Model #S9016, Sterling, Inc., Milwaukee, Wis., USA) able to maintain temperatures up to 230° C. was pre-cleaned to remove any polymeric or other residues and then thoroughly air dried for 2 hours before reattachment of the mixer bowl. The dry mixer was then preheated to 140° C. followed by a purge and then blanketing with anhydrous nitrogen a minimum flow during the course of the experiment. A foil package containing 740.7 grams of trimethylene carbonate was opened and the contents introduced followed by mixing at a speed setting of "6.5." After 10 minutes, stirring was stopped and 2.73 grams of a combination of 0.228 grams of $SnCl_2.2H_2O$ catalyst and 15.71 grams of diethylene glycol initiator was then added directly to the melted TMC. Mixing was recommended and after 10 minutes the temperature was raised to 160° C. which was then followed by an increase to 180° C. after 30 minutes. After an additional 30 minutes, 75 grams of glycolide monomer was added followed by an increase of the temperature to 200° C. After 15 minutes, 675 grams of glycolide were added and the temperature setting immediately changed to 220° C. After 40 minutes, the polymerized product was discharged at the 220° C. onto a clean release surface where it solidified as it cooled down to room temperature. The light brown polymer thus obtained was then packaged in a pyrogen free plastic bag and then mechanically granulated through a 4.0 mm screen prior to further analysis and processing.

In the '217 patent, Hayes additionally reported the inherent viscosity (IV) of this particular 50% PGA:50% TMC resin lot to be 0.99 dl/g.

A 50% PGA:50% TMC triblock co-polymer synthesized as described was then granulated as described in Example 1 and subsequently vacuum dried for at least 15 hours at 120° C. to 130° C. Approximately 250 grams of ground polymer was placed into the extruder described in Example 1 and heated to a die temperature of approximately 230° C. to 250° C. A random continuous precursor web material, approximately 3.2 inches (5.08 cm) in width, was acquired at a belt speed of approximately 20.4 cm/min (0.67 feet per minute). The precursor web material was morphologically similar to the unstretched 67:33-PGA:TMC precursor web material described in Example 1. The individual filaments formed cohesive bonds at contact points to form a self-cohered web. The filament diameter for web materials produced through this process ranged from twenty-five (25) microns to forty (40) microns. As noted in the '217 patent, these web materials typically have inherent viscosity values of 0.9 dl/g. Typical DSC values for these web materials are listed in Table 6.

TABLE 6

Typical DSC Values for Unset PGA:TMC (50:50) Precursor Web

| | $T_g/T_{odt}$ | $T_g/T_{odt}$ Capacity | Exotherm Peak | Exotherm Enthalpy | Melt Peak | Melt Enthalpy |
|---|---|---|---|---|---|---|
| Heat 1 | 5° C. | 0.5 J/g * ° C. | 110° C. | −33 J/g | 203° C. | 37 J/g |

Stretching of the unannealed, non-woven, self-cohered, precursor web material was conducted with the same equipment and uniaxial stretch rate as described in Example 1 for the 67:33-PGA:TMC triblock co-polymeric non-woven, self-cohered precursor web material. Care was taken that the unstretched precursor web was not exposed to combinations of heat or time that would lead to a substantial reduction of the web's crystallization exotherm enthalpy prior to stretching.

In addition to the uniaxial stretch ratios described in Example 1, additional uniaxial stretch ratios from 7:1 through 10:1 were performed. The oven temperature for zone one (1) was set at forty degrees centigrade (40° C.) and zone three (3) was set at eighty-five degree centigrade (85° C.). Thermal setting of the stretched web was accomplished after approximately one (1) minute in zone three (3) at eighty-five degrees centigrade (85° C.).

For webs of the present invention made with a 50:50 PGA:TMC triblock copolymer starting material, uniaxial stretch ratios of 7:1 through 10:1 produced webs with the most suppleness and uniform appearance.

Example 6

This example describes the formation of an article of the present invention using multiple layers of precursor web material and stretching the layered material sequentially in perpendicular directions.

A starting material was obtained by layering together nine sheets of unannealed, unstretched, precursor web material made according to Example 1. Each of the nine precursor sheets was produced at a belt speed of 1.58 ft/minute (48 cm/min). Each precursor sheet was found to have an area density of approximately 9.0 mg/cm² and a volume density of approximately 0.27 g/cc. Accordingly, nine layers of precursor sheet material would be expected to have an area density of approximately 81 mg/cm² and a volume density of approximately 0.27 g/cc.

The nine unannealed, unstretched, precursor web sheets were initially oriented so their width was generally in the same "machine direction" as the moving belt used to take up the web as it was formed. The similarly oriented layered sheets were stretched transversely (i.e., in a direction approximately 90 degrees from the direction of initial orientation of the unannealed web) in an oven with each of three heated zones set at ambient temperature, 50° C., and 120° C., respectively. The stretch ratio was 6:1 and the stretch rate was one foot per minute (30.5 cm/min).

The result was an article of the present invention having an area density of 18 mg/cm². This represents nearly a seventy-six (76) percent reduction in area density from the precursor web material. The article had a volume density of 0.11 g/cc. This represents nearly a sixty (60) percent reduction in volume density from the precursor web material (0.27 g/cc). The percent porosity of this web material was seventy-nine (79).

The percentage of elongation of the precursor web and the matrix tensile stress of the finished laminated web material was measured in the stronger cross-web direction and found to be sixty-four percent (64%) and 48 MPa, respectively. The percent elongation and matrix tensile stress of the finished laminated web material of the present invention, as measured in the weaker down-web direction, was found to be one hundred thirty-three percent (133%) and 5.2 MPa, respectively. Theses values are greater than those observed with the single layer uniaxially distended web of Example 1. Matrix tensile stress in the cross-web direction were also higher than the 22.7 MPa values reported in the '217 patent.

The layered web material of this example possessed increased suppleness and uniform appearance compared to a non-stretched, non-woven, self-cohered layered web material.

Example 7

This example describes materials produced from a first longitudinal web stretching procedure, followed by a subsequent transverse stretching procedure of the same web. This web material is referred to herein as a "Longitudinal-Transverse Stretched Web." Unannealed, unstretched, self-cohered precursor web material was prepared in accordance with Example 1 and processed as follows to form a material of the present invention. The precursor web material had an area density of approximately 45 mg/cm².

When evaluated using DSC parameters as described in Example 1, the thermal characteristics of both the utilized 67:33-PGA:TMC resin and the resulting unannealed precursor web were those summarized in Table 7.

TABLE 7

| | DSC Values for Unset 67:33 PGA:TMC Precursor Web | | | | | |
|---|---|---|---|---|---|---|
| 1 scan | $T_g/T_{odt}$ | $T_g/T_{odt}$ Capacity | Exotherm Peak | Exotherm Enthalpy | Melt Peak | Melt Enthalpy |
| Resin | 13.5° C. | 0.33 J/g * ° C. | none | none | 193° C. | 40.5 J/g |
| Web | 18.4° C. | 0.57 J/g * ° C. | 82.9° C. | −30.1 J/g | 196° C. | 39.5 J/g |

Five (5) varieties of stretched web material of the present invention were produced in this example based primarily on stretch ratio. Using a longitudinal stretching machine able to draw precursor web of suitable length across the surface of a supporting three zone heated metal sheet while moving in a longitudinal direction between dissimilar speed adjusted feed and take-up rollers, each unannealed, unstretched, precursor web material was first longitudinally stretched at a ratio of 1.5:1 at a temperature of twenty degrees centigrade (20° C.) in a direction substantially the same as the direction of the collector belt used for retrieval of the unstretched precursor web. This longitudinal direction (e.g., x-axis direction) is referred to herein as the "down-web" (DW) direction.

The longitudinally stretched unannealed, self-cohered, web material was then transferred to the heated platen transverse stretching machine described in Example 1. Each of these down-web stretched materials was subsequently stretched a second time in a "cross direction" (y-axis) perpendicular to the direction of the first longitudinal stretching procedure. This "cross-direction" stretching is referred to herein as "cross-web" (CW) stretching. The first sample (designated "1B") was stretched cross-web at a ratio of 2:1. The next sample ("2A") was stretched cross-web at a ratio of 3:1. Each remaining sample (2B, 2C, and 2D) was stretched cross-web at a ratio of 3.5:1, 4:1, and 4.5:1, respectively. The first and third heated zones in the oven were set to fifty degrees centigrade (50° C.) and one hundred twenty degrees centigrade (120° C.), respectively. The temperature in zone three was sufficient to completely heat-set the final stretched web material of the present invention. The resulting material was a fully annealed web, as is evidenced by the thermal characteristics displayed in Table 8 that displayed substantial DW extendibility.

TABLE 8

DSC Values for Longitudinal-Transverse 67% PGA:33% TMC Web

| 1 scan | $T_g/T_{odt}$ | $T_g/T_{odt}$ Capacity | Exotherm Peak | Exotherm Enthalpy | Melt Peak | Melt Enthalpy |
|---|---|---|---|---|---|---|
| 1B | 11.8° C. | 0.39 J/g * ° C. | none | none | 193° C. | 38.6 J/g |
| 2A | 11.4° C. | 0.35 J/g * ° C. | none | none | 192° C. | 38.9 J/g |
| 2B | 11.6° C. | 0.33 J/g * ° C. | none | none | 194° C. | 41.0 J/g |
| 2C | 11.1° C. | 0.30 J/g * ° C. | none | none | 192° C. | 38.8 J/g |
| 2D | 11.3° C. | 0.32 J/g * ° C. | none | none | 192° C. | 38.2 J/g |

The physical and tensile stress-strain properties of the (1.5:1) longitudinal-(4.5:1) transverse stretched web (2D), along with a fully set precursor web, are summarized in Table 9.

TABLE 9

Physical & Mechanical Properties of Longitudinal-Transverse 67:33 PGA:TMC Web

| | Tensile | | | Density | |
|---|---|---|---|---|---|
| Sample Description | Max Force (N) | Max Stress (MPa) | Matrix Stress (MPa) | Area (mg/cm²) | Volume (g/cm³) |
| Unstretched Precursor Web | 9.0 | 3.6 | 16.9 | 22.5 | 0.28 |
| Down Web Sample 2D - DW (3:2 DW by 5:1 CW) | 1.3 | 2.3 | 10.3 | 5.2 | |
| Cross Web Sample 2D - CW (3:2 DW by 5:1 CW) | 4.8 | 5.0 | 23.1 | 8.4 | |

Example 8

This example describes formation of two stretched self-cohered web materials of the present invention. The web materials were simultaneously stretched bi-axially in two directions (x-axis and y-axis) during processing.

An unstretched precursor web material was made according to Example 1. The TRANSVECTOR® apparatus was set at a spinneret angle of 8.5 degrees and a sweep rate of approximately 0.46 full cycles per second. The resulting unannealed, unstretched, precursor web material had a "usable width" of five (5) to six (6) inches (12.7 cm to 15.2 cm) with a web density of forty (40) to fifty (50) mg/cm² produced at a belt speed of approximately 8 cm/min. The unannealed, unstretched, precursor web material was not exposed to interim combinations of heat or time that would lead to a substantial reduction of the web's crystallization exotherm enthalpy.

A pantograph was used to biaxially stretch the unannealed precursor web material to form a first bi-axially stretched web material. A pantograph is a machine capable of stretching the precursor web material biaxially or uniaxially over a range of rates and temperatures (e.g., 50° C. to 300° C.). The pantograph used in this example was capable of stretching a piece of precursor web material from a four inch by four inch (4"×4") square piece to piece twenty-five inches by twenty-five inches (25"×25"). This represented a 6.1:1 stretch ratio in both x and y axes. To retain the precursor web material while stretching, the last half-inch of each arm on the pantograph was equipped with a pin array. There were a total of thirty-two (32) arms on the pantograph—seven on each side, plus one in each corner. The pantograph was also equipped with heated clamshell platens, which permitted control of the temperature of the precursor web material during processing.

The first bi-axially stretched web material was made by fixing a five (5) inch (12.7 cm) square piece of unannealed, unstretched, precursor web material (45 mg/cm²) onto the pantograph pin-frame at an initial setting of four inches by four inches (4"×4"). The clamshell platens were set at fifty degrees centigrade (50° C.) and were positioned over the unannealed web for two minutes to pre-heat the precursor web material in excess of the polymer's $T_{odt}$ prior to stretching. The pre-heated precursor web material was stretched sequentially at a ratio of 3.6:1 along the x-axis (down-web) and a ratio of 6.0:1 along the y-axis (transverse), both at a rate of 20 percent per second (20%/sec). Upon completion of the stretching process, the platens were retracted from the bi-axially stretched web material.

A pin frame, twelve (12) inches long by eight (8) inches wide, was inserted into the bi-axially stretched web material of the present invention to restrain a portion of it after it was removed from the pantograph pins. The bi-axially stretched web material was then heat-set, while restrained in the eight (8) inch by twelve (12) inch pin-frame, in an oven set at one hundred twenty degrees centigrade (120° C.) for about three (3) minutes. The resulting first biaxially stretched web material was removed from the pin-frame and the unrestrained portion trimmed away.

The first biaxially stretched web material was tested for area weight and thickness. From these measurements the volume density and porosity was calculated, as taught in Example 3. The area weight was measured as described in Example 1. The thickness was measured per the procedure in Example 1, except that a glass slide, 25 mm×25 mm×1 mm thick, was placed on the top of the web in order to clearly distinguish the upper surface of the web on the optical comparator. The area weight was 2.61 mg/cm², which represents about a ninety-four percent (94%) reduction of the unannealed precursor web material area weight. The thickness was 0.44 mm. These values give a volume density of 0.059 g/cm³ and a percent porosity of ninety-five (95). This percent porosity value is two-fold greater in void to solids ratio (void volume/solids volume) than the highest porosity disclosed in the '217 patent.

A second bi-axially stretched web material was made as described above except for modifications in several process parameter settings. For this second stretched web material, the preheat temperature was set to 70° C. and the unannealed web was pre-heated for about 30 seconds. The web was simultaneously stretched at a ratio of 3.6:1 along the x-axis and a ratio of 6.0:1 along the y-axis at the same stretch rate of thirty percent per second (30%/sec). The second bi-axially stretched web material was restrained and heatset on a pin-frame in an oven as described above for the first stretched web material.

The properties of the second bi-axially stretched web material were measured as described for the first stretched web material. The area weight was 3.37 mg/cm² and the thickness was 0.94 mm. This gave a volume density and porosity value of 0.036 g/cm³ and 97%, respectively. The void to solids ratio of the second bi-axially stretched web material is about 50% greater than the that of the first bi-axially stretched web material and about 3-fold greater than that disclosed in the '217 Patent.

Example 9

This example describes formation of a stretched web material of the present invention. The stretched web material has increased loft and suppleness and substantially resumes its original shape when an applied deforming force is removed.

A biaxially-stretched web material was made according to Example 8 except that a pin-frame was not used to restrain the web material as it was heat-set in the oven. Rather, the bi-axially stretched web material was suspended loosely in the oven from a rack as it was set. The bi-axially stretched web material was observed to contract after removal from the pantograph. The bi-axially stretched web material contracted further in the oven. The area of the fully stretched starting web material was reduced by about fifty percent (50%) with this process.

The resulting highly porous, bi-axially stretched and contracted, web material was thicker, softer, loftier, and more flexible than either similarly-produced stretched web material of Example 8. In addition, this bi-axially stretched and contracted web material resumed its original shape when an applied deforming force was removed. This resilient property was found in all portions of the bi-axially stretched and contracted web material. Microscopic examination (50×) of the resilient bi-axially stretched and contracted web material revealed highly curved self-cohered filaments of the material oriented in all directions, including the z-axis (i.e., perpendicular to the planar x and y axes). The diameter of these "z-axis oriented fibers" was similar to those of the "x-axis" and "y-axis" oriented fibers. The resulting highly porous, resilient, bi-axially stretched and contracted, self-cohered, bioabsorbable, polymeric web material of the present invention possessed physical and handling characteristics similar to fabrics commonly referred to as "fleece."

The properties of the bi-axially stretched and contracted fleece web material were determined per the methods described in Example 9 and are compared to the second biaxially stretched web of Example 8 in Table 10 below:

TABLE 10

| Property | Example 9 | Example 8 |
|---|---|---|
| Area Weight (mg/cm²) | 5.13 | 3.37 |
| Thickness (mm) | 2.11 | 0.94 |
| Volume Density (g/cm³) | 0.024 | 0.036 |
| Porosity (%) in the absence of additional components | 98 | 97 |
| Void/Solids Ratio | 49 | 32 |

FIG. 4 is a scanning electron micrograph (SEM) showing filaments of these materials oriented in multiple directions following the stretching process. Under ten-times (10×) magnification, a number of the filaments appeared to be oriented in a direction perpendicular (z-axis) to the other filaments oriented along the x and y axes of the material. On visual inspection, the thicker articles of the present invention had a fleece-like appearance having a deep pile, high degree of loft, and very high percent porosity.

Example 10

This example describes the formation of articles of the present invention by stretching precursor web material radially in all directions simultaneously. Both single and multiple layered precursor web materials were radially stretched in this example. In some embodiments, these multiple layered precursor web materials became laminated together in the finished web material.

In each embodiment, at least one piece of a 67:33-PGA:TMC precursor web material made according to Example 1 was cut into circular pieces having an initial diameter of six (6) inches (15.24 cm). Embodiments utilizing multiple layers of precursor web material were formed by placing several layers of the precursor web material together prior to cutting. For each embodiment, the circular material was restrained in a clamping apparatus capable of stretching the precursor web material in all directions at an equal rate within a temperature controlled environment.

In each embodiment, eight clamps were placed equidistant around the periphery of the particular precursor web material approximately one-half (0.5) inch in from the edge of the web material. This effectively reduced the initial diameter of the precursor web material from six (6) inches to five (5) inches (12.7 cm). The clamped precursor web material was pre-heated at a temperature of 50° C. for approximately two (2) minutes to raise the precursor web material above the order-disorder temperature ($T_{odt}$) of the particular polymer system used to make the precursor web material. The softened precursor web material was then stretched at a rate of 0.25 inches/second until the web had a diameter of twelve (12) inches (30.48 cm). The four-layered material was stretched to a final diameter of 14 inches (35.56 cm) at the same stretch rate. While retained in the stretched configuration, the stretched web material was heated to 120° C. for two (2) to three (3) minutes to heat-set the stretched web material.

The parameters of layers, precursor web material area weights, and stretch ratios (final diameter/initial diameter) of each article are listed in Table 11, below. The total area weight of the precursor web material is the product of the precursor layer area weight and the number of layers. For example, the gross precursor area weight of article 10-2 was about 90 mg/cm² (2 layers×45 mg/cm²). Article 10-6 was produced to a uniform appearance, but was not quantitatively tested. Also listed in the table is the area weight of the finished stretched web.

TABLE 11

| Article ID | Layers | Precursor Layer Area Weight (mg/cm²) | Stretch Ratio | Area Weight of Stretched Web (mg/cm²) |
|---|---|---|---|---|
| 10-1 | 1 | 45 | 2.8 | 3.68 |
| 10-2 | 2 | 45 | 2.4 | 9.43 |
| 10-3 | 2 | 22 | 2.8 | 5.87 |
| 10-4 | 2 | 10 | 2.8 | 2.75 |
| 10-5 | 4 | 10 | 2.8 | 5.40 |
| 10-6 | 6 | 45 | 2.4 | Not measured |

FIG. 4A is a scanning electron micrograph (SEM) showing filaments of a radially stretched self-cohered web material of the present invention. The image, which depicts filaments oriented radially in multiple directions following the stretching process, is of an alternative embodiment fabricated from 50% PGA:50% TMC copolymer.

Example 11

This example provides a compilation of porosity values observed in various embodiments of the present invention. Initially, precursor web materials as described in Example 1 were prepared at belt speeds of 7.9, 14.0, 20.4, and 48.0 cm/min, annealed under restraint, and then evaluated for volume density and percent porosity. The percent porosity values were determined by controlling the height of the finished web material with a glass microscope slide and an optical comparator as described in Example 8. Stretched web materials of the present invention having the highest percent porosity values were obtained with a belt speed of 48.0 cm/min.

Appropriately sized samples of precursor web materials were either transversely stretched as described within Example 1 or bi-axially stretched as described in either Example 8 or 9. The precursor web material and several finished stretched web materials were then evaluated for average percent porosity. The percent porosity results and accompanying processing parameters are presented in Table 12. As seen from Table 11, the highest percent porosity possessed by the precursor web material was 89.7%. Accordingly, all stretched, self-cohered, web materials of the present invention have percent porosity values of at least ninety percent (90%).

TABLE 12

Porosity of Various Precursor and Stretched Web Structures

| BS | Belt Speed (cm/min) | Stretch Ratio Transverse or y-axis | x-axis | Percent porosity in the absence of additional components | Fabrication Method (Example #) |
|---|---|---|---|---|---|
| Precursor | 48 | n.a. | n.a. | 89.7 | 1 |
| Biaxial | 7.9 | 6:1 | 3.6:1 | 97.3 | 8 |
| Biaxial | 20.4 | 6:1 | 3.6:1 | 96.8 | 8 |
| Biaxial-Fleece | 7.9 | 6:1 | 3.6:1 | 98.1 | 9 |
| Uniaxial | 7.9 | 5:1 | | 89.8 | 1 |
| Uniaxial | 7.9 | 6:1 | | 90.7 | 1 |
| Uniaxial | 7.9 | 7:1 | | 91.8 | 1 |
| Uniaxial | 13 | 5:1 | | 92.5 | 1 |
| Uniaxial | 13 | 6:1 | | 92.7 | 1 |
| Uniaxial | 13 | 7:1 | | 90.9 | 1 |
| Uniaxial | 14 | 6:1 | | 94.0 | 1 |
| Uniaxial | 20 | 4:1 | | 90.7 | 1 |
| Uniaxial | 20 | 5:1 | | 92.2 | 1 |
| Uniaxial | 20 | 6:1 | | 93.2 | 1 |
| Uniaxial | 20 | 8:1 | | 94.4 | 1 |
| Uniaxial | 48 | 5:1 | | 94.6 | 1 |

As seen in Table 12, the percent porosity increased for all embodiments of the stretched web material of the present when compared to precursor web materials made by the present inventors to have as high a percent porosity as possible with currently available technology.

Example 12

This example describes the formation of an article of the present invention in a tubular form (FIG. 13).

In this example, a tubular article able to stretch in a radial direction was formed utilizing a mandrel combination equipped with means for longitudinal extension of a wrapped tube formed from an unset precursor web. The utilized combination is composed of a smaller rigid rod or tube ("mandrel") that can be at least partially contained within the inside diameter of a circumferential means for affixing the ends of the wrapped tube. At least one end of the tube is then slid by manual or mechanical means along the axis of the mandrel to effect the desired longitudinal expansion ratio. Alternatively, once the tube is formed and attached to the circumferential fixation, the mandrel can be removed and expansion accomplished through tensile extension.

Articles were formed by wrapping an approximately five inch (12.7 cm) length of an unannealed precursor web material (~9 mg/cm$^2$) made as described within Example 1 around both a three-eighths inch (0.953 cm) diameter metal mandrel and a portion of the circumferential fixation sufficient to allow later physical attachment. Wrapping was achieved by slightly overlapping the opposing edges to form a "cigarette wrap." This step was repeated with offset seams to produce a multi-layered (i.e., 2-10 layers (5 layers preferred)) tube of unannealed precursor web material.

Attachment of the tube to the fixation means was accomplished by affixing the overlying ends of the tube against the circumferential ridge with a copper wire. The combination was then placed in a preheated oven set at a temperature of 50° C. for approximately two (2) minutes to soften the unset polymeric material. The softened material was then stretched longitudinally at a ratio of approximately 5:1. This was followed by fixing the sliding mandrel in place heating the combination to 100° C. for five (5) minutes to set (i.e., anneal or fully crystallize) the final article.

This tubular form of the present invention displayed an ability to change from an initial first diameter to a larger second diameter when exposed to radial expansion forces. The tube formed in this example was found to be readily distensible from a first diameter to a second diameter approximately two times larger than the first diameter.

Example 13

This example describes the formation of an article of the present invention in a tubular form having an ability to increase in diameter from a first initial diameter to a second larger diameter, combined with an ability to change axial length (FIG. 17).

As in the prior example, this article was formed by cigarette wrapping multiple layers of unannealed web around both a three-eighths inch (0.953 cm) diameter metal mandrel and circumferential fixation. The wrapped combination was then placed in an oven preheated at a set temperature of 50° C. for approximately two (2) minutes to soften the unannealed polymeric material. The softened material was then stretched longitudinally at a ratio of 5:1, the sliding fixation immobilized, and the combination heated for 1 minute in an oven set to 100° C. The combination was removed and opposite ends of the now stretched tubular form were urged toward each other to a length approximately half that if the original extension distance so as to compact the material along its length in an "accordion-like" fashion. The combination containing this "corrugated" tubular material was then heated to 130° C. for five (5) minutes to impart a complete set to the final article. Upon completion and removal of the article from the fixation, the article was observed to retain the corrugated structure, evidencing partial crystallization at the 100° C. treatment conditions.

In addition to having the ready ability to change diameter when exposed to radial expansion forces, the article described in this example was also able to change in length. In addition, this article was more flexible and exhibited greater resistance to kinking when bent into a curved conformation than the article described in the previous Example, supra.

Example 14

Figure 16:
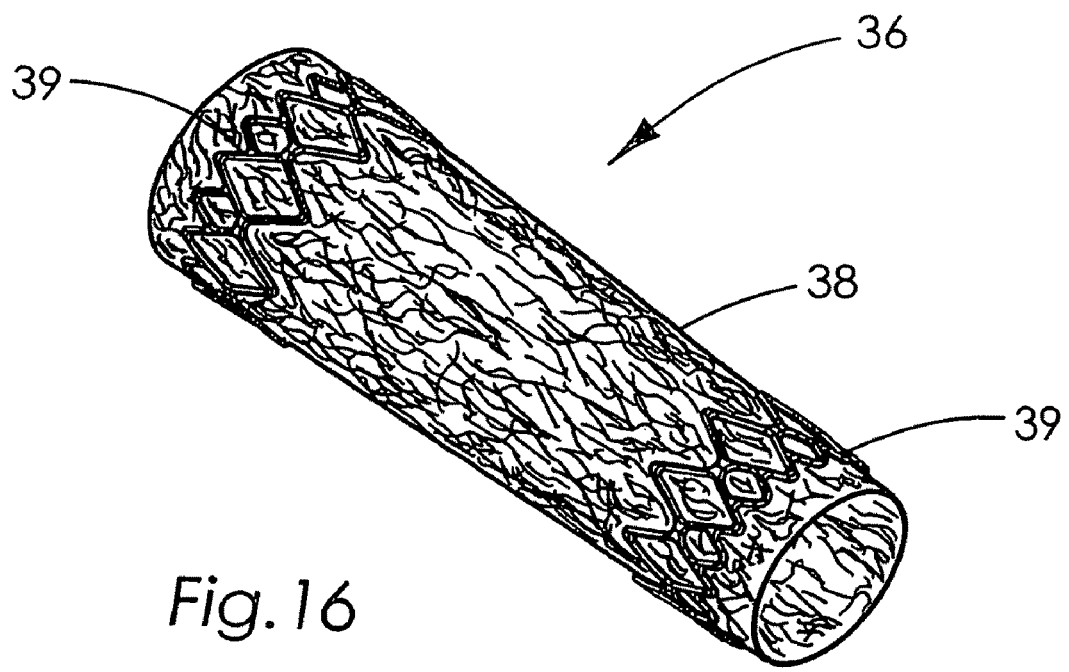
FIG. 16 is an illustration of a web material of the present invention in a tubular form with at least one structural element included therewith.

This example describes the formation of an article of the present invention in a tubular form having at least one framework component incorporated into the article (FIG. 16).

A two layered fully set first tubular form was constructed as described in Example 12, trimmed to approximately four inches in length, and then left on the mandrel without overlapping onto the circumferential fixation. A 0.020 inch (0.051 cm) diameter copper wire was then wound in a helical manner around the outer surface of the tubular form with approximately 0.25 inch (0.635 cm) spacing between windings. A second tubular form made of precursor web material approximately 5 inches (12.7 cm) wide was then closely wrapped over both the wire-wound first tubular form and a portion of the circumferential fixation sufficient to allow its physical attachment. The combination was then wrapped with an overlying sacrificial polytetrafluoroethylene (ePTFE) pipe-tape style film. Longitudinal stretching of the tubular form was then undertaken as previously described at a 5:1 stretch ratio to effect tube extension simultaneous with a reduction of the tubes inner diameter. This process effectively compressed the outer tube into intimate contact with the underlying metallic coil and inner tube. This wrapped construct was then heated to 100° C. for five (5) minutes to heatset the article. The sacrificial PTFE film was removed from the finished article.

The article thus produced was a metallic coil encased within both overlying and underlying layers of a flexible stretched, non-woven, self-cohered PGA:TMC tube. This construction could serve as an implantable intravascular medical device, such as a stent or stent graft.

Example 15

Figure 14:
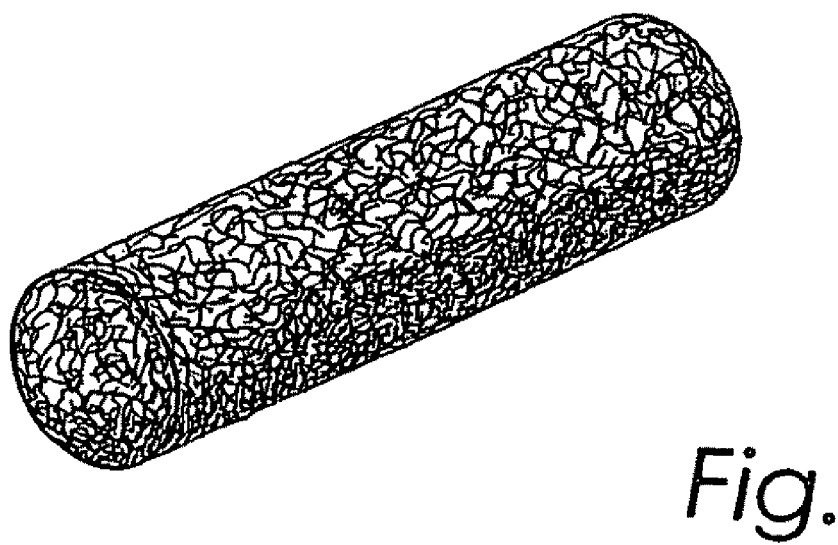
FIG. 14 is an illustration of a web material of the present invention having a cylindrical form.

This example describes the formation of a stretched self-cohered web material of the present invention in the form of a rope or flexible rod (FIG. 14).

In this example, a stretched rope or flexible rod self-cohered filamentous form was formed by longitudinally pulling and axially twisting a length (2.54 cm wide×25.4 cm long) of unannealed, unstretched, precursor web material (9 mg/cm$^2$) to a point of tactile resistance. The length of precursor material was extended approximately 15.25 cm (6 inches) and twisted approximately ten (10) times. The material was then stretched along its longitudinal axis at a stretch ratio greater than 2:1. In this example the precursor web material was both twisted and stretched by manual means, but mechanical methods may be also be used.

The article was then restrained in its twisted form and heated in an oven set to a temperature of 50° C. for 1 minute, removed, and then promptly stretched along its longitudinal axis to a distance twice that of its original length. The article was then restrained in its stretched form and then heated in an oven set to 100° C. for 5 minutes to heatset (i.e., anneal or fully crystallize) the final article.

The finished article appeared to be a highly flexible rod or rope that visually appeared to possess a continuous pore structure through its cross section.

Example 16

This example describes the formation of a web material of the present invention having a very low volume density and very high percent porosity (FIG. 19).

While a porous stretched web material from any of the above-described examples is suitable for use as a starting material for this very high percent porosity material, a web material made according to Example 1 at a 6:1 stretch ratio and an area density of 40-50 mg/cm$^2$ was obtained and used as the starting web material in this example.

The starting web material was subjected to a carding procedure by laying the web material flat onto a granite surface plate, restraining the web material by hand, and repeatedly abrading the filaments of the web material in a random fashion with a wire brush. As the filaments of the web material were abraded, at least some of the filaments of the web were engaged and separated by the wires of the brush. As the filaments were separated, the percent porosity of the web material increased and the volume density decreased. The visual appearance of the finished carded web material was similar to a "cotton ball."

Figure 19A:
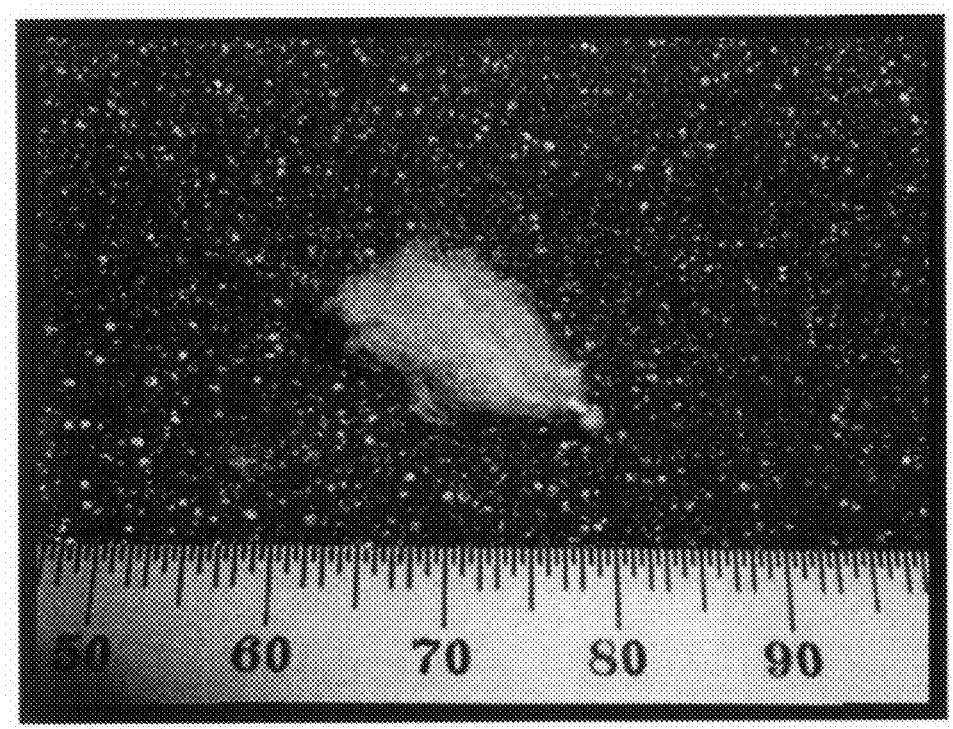
FIG. 19A is a photograph of a web material of the present invention having a very high degree of porosity and a metallic band attached thereto.
Figure 19B:
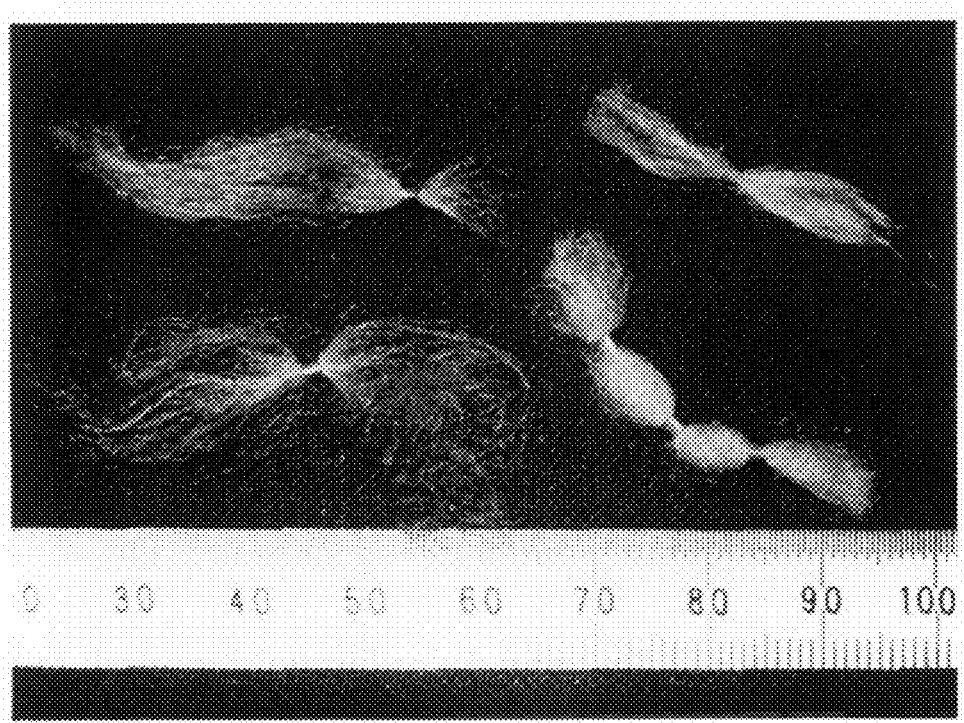
FIG. 19B is a photograph of a web material of the present invention having a very high degree of porosity with multiple metallic bands attached thereto.
Figure 20:
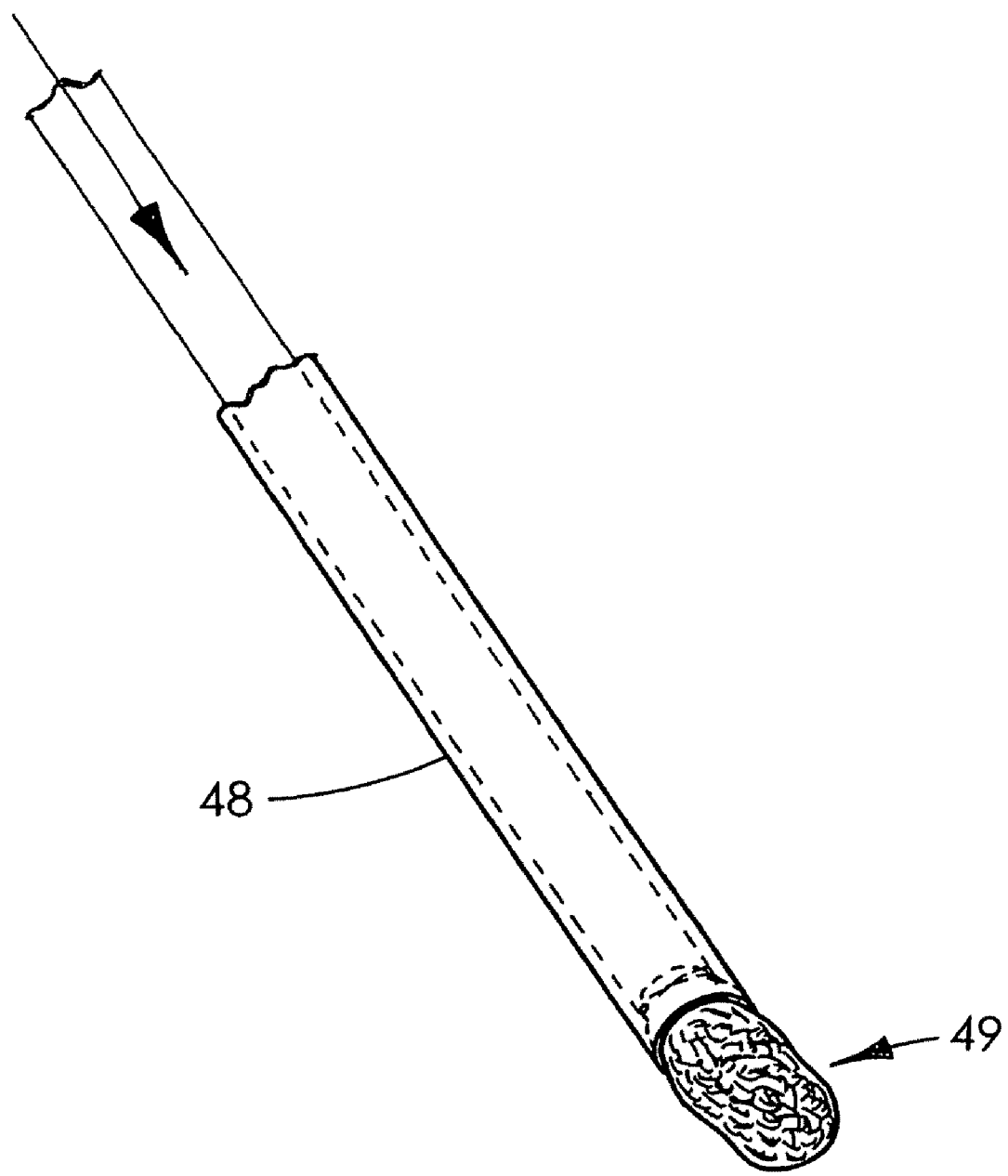
FIG. 20 is an illustration of the web material of FIG. 19 placed inside a delivery device.

In another embodiment, at least one metallic band is attached to the web material (FIGS. 19A and 19B). The metallic bands can serve as radio-opaque markers to aid in visualizing the web material during and after implantation.

As described in Example 17, this material has been shown to be thrombogenic and provide hemostasis in a variety of circumstances. For example, the carded web material of the present invention can stop, or significantly reduce, bleeding at an incision site in a major blood vessel, such as a femoral artery. Bleeding can also be stopped or significantly reduced in puncture wounds, lacerations, or other traumatic injuries. The carded web material described in this example can also be used to fill an aneurysm or occlude a blood vessel or other opening in the body of an implant recipient.

The highly porous web material described herein can be combined with a delivery system (FIG. 20), such as a catheter, to aid in placement of the web material at an indirectly accessible anatomical site.

This web material can also be used as a component of an implantable medical device to assist in providing a liquid seal for the device against an anatomical structure or tissue.

Example 17

This example describes the use of a very highly porous web material of the present invention to stop bleeding in an artery of an implant recipient.

Using a domestic porcine model that had previously been heparinized, an eight French (BF) guiding catheter was used to selectively access the cranial branch of the left renal artery. An angiogram was performed for baseline imaging and the guide wire removed. A 6F guide catheter containing a combination of an approximately 7 mm diameter by 20 mm long piece of web material made according to Example 16 was then introduced into the vasculature of the implant recipient through the length of the 8F catheter. The web material of Example 16 contained a radio-opaque marker band to assist in remotely visualizing the present invention during and after implantation (FIG. 20).

The marked web material of Example 16 was then deployed into the cranial branch of the above-mentioned left renal artery from the 6F catheter. Following implantation of the marked web material in the renal artery, partial occlusion of the blood vessel was observed, via angiogram, within thirty seconds. Full occlusion of the blood vessel was observed at three (3) minutes post deployment. Occlusion was interpreted to be caused by coagulation of blood in the vessel at the implantation site, despite the presence of the heparin.

A second procedure was performed on this implant recipient to demonstrate the ability of the web material of Example 16 to stop blood flow at an arterial incision site. A femoral laceration was created with a partial transaction of the femoral artery. The artery was occluded proximally, so only retrograde flow was present. Despite this condition bleeding at the incision site was profuse. Two cotton ball size pieces of the web material of Example 16 were then applied to the arteriotomy and held under digital pressure for approximately 30 seconds. Though there was some initial seeping of blood through the ball, the bleeding was completely stopped at two minutes.

Example 18

Swine and canine with normal activated clot times (ACT) used for other acute vascular patency studies were used in this Example for a model of an organ laceration injury. In order to induce organ laceration, a 13 mm diameter puncture was made in the liver or spleen of the implant recipient with a modified trephine. The puncture was allowed to bleed freely for forty-five (45) seconds. Approximately 1 gram of the highly porous web material described in Example 16 was applied by hand into the puncture with compression for one (1) minute. Pressure was then released and the wound evaluated for bleeding. If bleeding did not cease, pressure was re-applied for another minute and the evaluation repeated.

As a comparison, a commercially available chitosan-based haemostatic material (HEMCON; HemCon Inc., Portland, Oreg.) was examined in the same organ laceration model. Both the highly porous web material described in Example 16 and the HEMCON material successfully produced haemostasis after 1 minute compression. The ease of handling and implantation of the present invention was considered superior to the HEMCON product.

Though the web material of Example 16 is in a "cotton ball-like" form, other forms of the highly porous web material can be used for hemostasis and other medical circumstances requiring thrombogenic results. These forms include, but are not limited to, rolls or wads of the web material. The high compressibility of the present invention allows for efficient packaging of the invention.

Example 19

This example demonstrates the thrombogenic properties of the present invention through the use of a comparative in vitro blood clotting test providing results expressed in terms of relative clot time (RCT).

To determine an in vitro whole blood clot time for samples of different thrombogenic materials, approximately two (2) mg of each test sample material was obtained and individually placed in a polypropylene microcentrifuge tube. The sample materials used in this test were porous web materials made according to Examples 1 and 16, and two commercially available hemostatic materials, HEMCON® chitosan bandage (HemCon Inc., Portland, Oreg.) and HEMABLOCK® hemostatic agent microporous polysaccharide beads (Abbott Laboratories, Abbott Park, Ill.).

Figure 18:
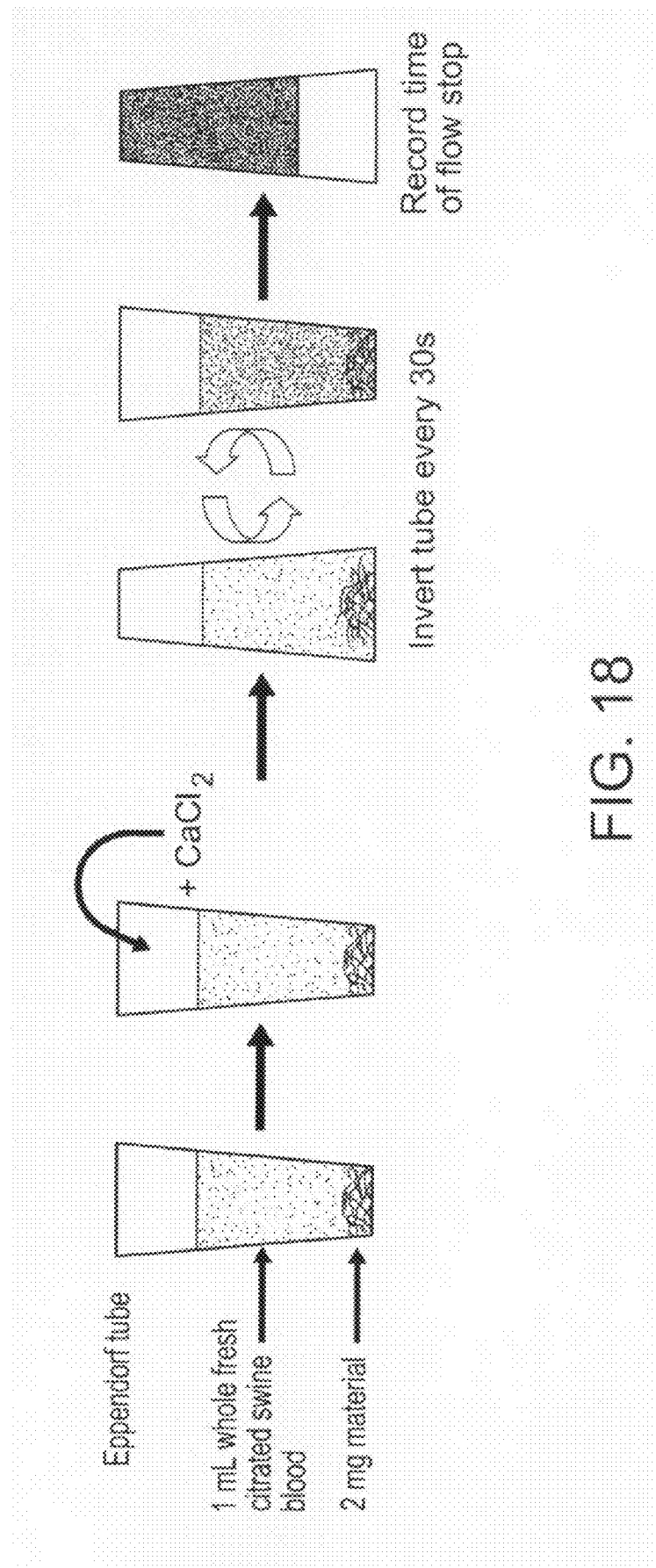
FIG. 18 is an Illustration of a whole blood coagulation time assay.

FIG. 18 illustrates the steps followed for the Relative Clot Time test. In the test, fresh unheparinized arterial blood was collected from domestic swine and immediately mixed with sodium citrate to a final citrate concentration of 0.0105 M. One (1) ml of the fresh citrated blood was added to each sample tube. To facilitate the clotting cascade, 100 µl of 0.1M calcium chloride was added to each sample tube. The tubes were immediately capped and inverted 3 times. At each 30 second interval, the tubes were inverted for 1 second and returned to their upright positions. The time was recorded when blood ceased to flow in a sample tube. Each test included a positive control (calcium+citrated blood only) and negative control (citrated blood only). For every test, clot time was normalized to the calcium control, with the smaller value indicating a faster overall time to clot.

The web materials made according to both Example 1 and Example 16 each reduced the Relative Clot Time (RCT) to a value of approximately 0.7 when compared to the positive citrated calcium control value of 1.0. These materials also displayed superior results to the commercially available hemostatic products HEMCON, with an experimentally observed RCT of 1.0. With the HEMABLOCK® hemostatic agent powder an RCT of 0.9 was observed.

Example 20

This example describes the formation of an article of the present invention to include a second bioabsorbable polymeric material (FIG. 9).

In this Example, a finished 6:1 web material according to Example 1 was obtained and imbibed with a film made of carboxymethylcellulose (CMC). The CMC utilized was of the high viscosity (1500-3000 cps at one percent (1%) at twenty-five degrees centigrade (25° C.)) variety available from Sigma-Aldrich (St. Louis, Mo., USA), Catalog #C-5013. A CMC film was formed from a gel concentration of 8 g CMC/100 ml distilled water (8% w/v). The film had a thickness approximately equal to the thickness of the web material to be imbibed. The film was produced by rolling a bead of 8% CMC gel onto a flat metal plate and allowing the film to consolidate. The CMC gel film was then placed in contact with a similarly sized piece of web material from Example 1 and tactilely pressed together between two suitable release surfaces for approximately one (1) minute at room temperature. The CMC-imbibed web material was then dried under vacuum at 40° C., with an occasional purge with air.

This process was repeated with CMC gel film placed on both sides of the web material in a "sandwich" relationship.

When wetted with saline, water, or blood, the material described in this example generated a concentrated gel that displayed significant adherence that made the web readily conformable to the topography of many physical features. Such adherence was recognized as carrying potential to assist a surgeon, interventionalist, or other healthcare professional in temporarily maintaining the present invention at a particular anatomical location, implantation site, or in approximation to a surgical instrument or other implantable device. The CMC coating in either dry or gel form may affect the permeation rate of various physiological fluids into or out of the underlying web material.

Example 21

This example describes imbibing carboxymethylcellulose (CMC) into interstitial spaces of a finished 7:1 web material according to Example 5, supra. To make this construction, high viscosity sodium carboxymethylcellulose ("CMC"; Sigma Chemical Company, St. Louis, Mo.) was dissolved in deionized water at a four percent (4%) concentration (i.e., 4 g/100 ml) using an industrial blender. Entrapped air was removed by centrifugation. The CMC solution was imbibed into the finished web material (3.8 cm×10.2 cm) using a roller to completely fill the porosity of the web. The CMC-imbibed web was air dried at room temperature for sixteen hours (16 hrs) to produce a CMC-imbibed, self-cohered, stretched PGA:TMC web material.

When wetted with saline, water, or blood, the material described in this example generated a concentrated gel that displayed significant adherence that made the web material readily conformable to the topography of many physical features. Such adherence was recognized as carrying potential to assist a surgeon, interventionalist, or other healthcare professional in temporarily maintaining the present invention at a particular anatomical location, implantation site, or in approximation to a surgical instrument or other implantable device.

Example 22

This example describes imbibing carboxymethylcellulose (CMC) into interstitial spaces of a finished web according to Example 16 and dissolving the imbibed CMC from the web into a phosphate buffer saline (PBS) solution. To make this construction, 4% CMC was imbibed into a sample of highly porous web material made according to Example 16 using a roller to completely fill the void spaces. The imbibed web was air dried at room temperature for sixteen hours (16 hrs) to produce a CMC-imbibed high porosity, self-cohered, PGA:TMC web material. The CMC-imbibed web of Example 16 was then immersed in a PBS solution. Upon immersion, the CMC swelled to produce a hydrogel-filled, high porosity, self-cohered PGA:TMC web material. Upon immersion for an additional ten (10) minutes, the CMC appeared to dissolve into the PBS and elute from the web material.

Example 23

This example describes imbibing a carboxymethylcellulose (CMC) into interstitial spaces of a web material according to Example 16. To make this construction, eight percent (8%) CMC solution was imbibed into a sample of highly porous web material made according to Example 16 using a roller to completely fill the void spaces of the highly porous web material. The imbibed web was then dried under vacuum at 40° C. to produce a CMC-imbibed high porosity, self-cohered, PGA:TMC web material. Upon immersion into PBS, the CMC swelled to produce a hydrogel-filled web. Upon additional immersion for 10 min, the CMC dissolved and eluted from the web material.

Example 24

This example describes imbibing carboxymethylcellulose (CMC) into interstitial spaces of a web material according to Example 21 and cross-linking the CMC to itself within the web material. To make this construction, a finished material according to Example 21 was obtained and subjected to chemical cross-linking as taught in U.S. Pat. No. 3,379,720, issued to Reid, and incorporated herein by reference. In this process, the pH of the four percent (4%) CMC solution was adjusted to pH 4 with dropwise addition of thirty-seven percent (37%) HCl. Once the CMC was imbibed and air dried according to Example 20, the composite was placed in an oven set at one hundred degrees centigrade (100° C.) for one (1) hour to induce ester crosslinks between carboxylic acid groups and alcohol groups present on the CMC chemical backbone. The result was a high porosity, self-cohered, stretched PGA:TMC web material with a cross-linked CMC material contained therein.

Example 25

This example describes swelling the cross-linked CMC web material of Example 24 in PBS. The material of Example 24 was immersed into PBS for several minutes. Upon immersion, the CMC swelled to produce a hydrogel-filled web. Upon additional immersion for two (2) days, the cross-linked chemical groups of the CMC material caused the CMC to be retained within the web. Once filled with a cross-linked hydrogel, the web material did not permit PBS to flow therethrough. The web material of this embodiment functioned effectively as a fluid barrier.

Example 26

This example describes imbibing polyvinyl alcohol (PVA) into interstitial spaces of a finished 7:1 web according to Example 5. To make this construction, USP grade polyvinyl alcohol (PVA) was obtained from Spectrum Chemical Company, (Gardena, Calif.). The PVA was dissolved in deionized water at a ten percent (10%) concentration (i.e., 10 g/100 ml) using heat and stirring. Entrapped air was removed by centrifugation. The PVA solution was imbibed into a web material (3.8 cm×10.2 cm) according to Example 5 using a roller to completely fill the void spaces of the highly porous web. The imbibed web was air dried at room temperature for sixteen hours (16 hrs) to produce a PVA-imbibed, self-cohered, PGA:TMC web material.

Example 27

This example describes imbibing polyvinyl alcohol (PVA) into interstitial spaces of a web according to Example 26 and dissolving the PVA from the web into a phosphate buffer saline (PBS) solution. The PVA-imbibed web material of Example 26 was immersed in a PBS solution. Upon immersion, the PVA swelled to produce a hydrogel-filled, self-cohered, stretched PGA:TMC web material. Upon immersion for an additional ten (10) minutes, the PVA dissolved into the PBS and eluted from the web material.

Example 28

This example describes cross-linking a PVA-imbibed material according to Example 26 with succinic acid. Once PVA was imbibed into a web material according to Example 26, the PVA was chemically cross-linked with succinic acid, a dicarboxylic acid, according to the teachings of U.S. Pat. No. 2,169,250, issued to Izard, and incorporated herein by reference.

PVA was dissolved in deionized water at a 10% concentration (i.e., 10 g/100 ml) using heat and stirring. Succinic acid (Sigma) was also dissolved in the PVA solution at a concentration of 2 g per 100 ml. Entrapped air was removed by centrifugation. The PVA-succinic acid solution was imbibed into a 7:1 web material (3.8 cm×10.2 cm) according to Example 5 using a roller to completely fill the void spaces of the highly porous web. The web material was air dried at room temperature for sixteen hours (16 hrs). The composite was placed in an oven set at one hundred forty degrees centigrade (140° C.) for fifteen (15) minutes to induce ester crosslinks between carboxylic acid groups present on the succinic acid and alcohol groups present on the PVA.

Example 29

This example describes cross-linking a PVA-imbibed material according to Example 26 with citric acid. Once PVA was imbibed into a web according to Example 26, the PVA was chemically crosslinked with citric acid, a tricarboxylic acid, according to the teachings of U.S. Pat. No. 2,169,250, issued to Izard, and incorporated herein by reference.

PVA was dissolved in deionized water at a 10% concentration (i.e., 10 g per 100 ml) using heat and stirring. Citric acid (Sigma) was also dissolved in the PVA solution at a concentration of 2 g per 100 ml. Entrapped air was removed by centrifugation. The PVA-citric acid solution was imbibed into a 7:1 web material (3.8 cm×10.2 cm) according to Example 5 using a roller to completely fill the void spaces of the highly porous web material. The web material was air dried at room temperature for sixteen hours (16 hrs). The composite was placed in an oven set to one hundred forty degrees centigrade (140° C.) for fifteen (15) minutes to induce ester crosslinks between carboxylic acid groups present on the citric acid and alcohol groups present on the PVA.

Example 30

This example describes cross-linking a PVA-imbibed material according to Example 26 with aspartic acid. Once PVA was imbibed into a web according to Example 26, the PVA was chemically crosslinked with aspartic acid, a dicarboxylic amino acid.

PVA was dissolved in deionized water at a 10% concentration (i.e., 10 g/100 ml) using heat and stirring. Aspartic acid (free acid, Sigma) was also dissolved in the PVA solution at a concentration of 1 g per 100 ml. Entrapped air was removed by centrifugation. The PVA-aspartic acid solution was imbibed into a 7:1 web material (3.8 cm×10.2 cm) according to Example 5 using a roller to completely fill the void spaces of the highly porous web material. The web material was air dried at room temperature for sixteen hours (16 hrs). The composite was placed in an oven set to one hundred forty degrees centigrade (140° C.) for fifteen (15) minutes to induce ester crosslinks between carboxylic acid groups present on the aspartic acid and alcohol groups present on the PVA.

Example 31

This example describes cross-linking a PVA-imbibed material according to Example 26 with carboxymethylcellulose (CMC). Once PVA was imbibed into a web according to Example 26, the PVA was chemically crosslinked with CMC, a polycarboxylic acid.

PVA was dissolved in deionized water at a 10% concentration (i.e., 10 g/100 ml) using heat and stirring. CMC was also dissolved in the PVA solution at a concentration of 1 g per 100 ml. In this process, the pH of the one percent (1%) CMC solution was adjusted to pH 1.5 with dropwise addition of thirty-seven percent (37%) HCl. Entrapped air was removed by centrifugation. The PVA-CMC acid solution was imbibed into a 7:1 web material (3.8 cm×10.2 cm) according to Example 5 using a roller to completely fill the void spaces of the highly porous web material. The web material was air dried at room temperature for sixteen hours (16 hrs). The composite was placed in an oven set to one hundred forty degrees centigrade (140° C.) for fifteen (15) minutes to induce ester crosslinks between carboxylic acid groups present on the CMC and alcohol groups present on the PVA.

Example 32

This example describes swelling the hydrogel component of the constructions of Examples 28-31 in PBS. Upon immersion of each of these constructions in a PBS solution, the PVA swelled to produce hydrogel-filled web materials of the present invention. Upon additional immersion for two (2) days, the PVA was intact within all web materials due to the presence of the above-mentioned chemical cross-linkages. Each hydrogel-filled web material was observed to prevent movement of PBS across the web material.

Example 33

This example describes imbibing PLURONIC® surfactant into interstitial spaces of a web material according to Example 5. PLURONIC® surfactant is a copolymer of polyethylene glycol and polypropylene glycol, available from BASF (Florham Park, N.J.). Certain grades of PLURONIC® surfactant form gels when immersed in warm biological fluids, such as grade F-127, as taught in U.S. Pat. No. 5,366,735, issued to Henry and incorporated herein by reference. Grade F-127 PLURONIC® surfactant was dissolved in dichloromethane at a concentration of 5 g per 5 ml.

The F-127 solution was imbibed into a 7:1 web material (3.8 cm×10.2 cm) according to Example 5 using a roller to completely fill the void spaces of the highly porous web material. The imbibed web material was dried at sixty degrees centigrade (60° C.) for five (5) minutes. The imbibed web material was immersed in PBS, prewarmed to 37° C. Upon immersion, the F-127 swelled to produce a hydrogel-filled web material. Upon immersion for an additional 1 day at 37° C., the F-127 dissolved and eluted from the web material.

Example 34

This example describes the incorporation of a bioactive species into the hydrogel material of a web material according to Example 21 (FIG. 9A). Dexamethasone (Sigma, St. Louis) was dissolved at a concentration of 10 mg/100 ml in deionized water. Four grams of high viscosity CMC was added to the solution using an industrial blender. Entrapped air was removed by centrifugation. The CMC/dexamethasone solution was imbibed into the finished web using a roller, and was air dried at room temperature for 16 hrs. Upon immersion into PBS, the CMC swells and the dexamethasone was observed to elute from the hydrogel.

Example 35

This example describes the incorporation, with physical crosslinking, of a bioactive species into the hydrogel material of a web material according to Example 21. Dexamethasone phosphate (Sigma, St. Louis) was dissolved at a concentration of 10 mg/100 ml in deionized water. Four grams of high viscosity CMC was added to the solution using an industrial blender. Entrapped air was removed by centrifugation. The CMC/dexamethasone phosphate solution was imbibed into the finished web using a roller, and was air dried at room temperature for 16 hrs. Upon immersion into PBS, the CMC swells and the dexamethasone phosphate was observed to elute from the hydrogel, at a rate slower than in Example 34, due to physical acid/base complexation between the basic dexamethasone phosphate and the acidic CMC.

Example 36

This example describes the incorporation, with chemical crosslinking, of a bioactive species into the hydrogel material of a web material according to Example 24. Dexamethasone (Sigma, St. Louis) was dissolved at a concentration of 10 mg/100 ml in deionized water. Four grams of CMC was added to the solution using an industrial blender. The pH of the dexamethasone/CMC solution was adjusted to pH 4 with dropwise addition of thirty-seven percent (37%) HCl. Once the dexamethasone/CMC solution was imbibed and air dried according to Example 20, the composite was placed in an oven set at one hundred degrees centigrade (100° C.) for one (1) hour to induce ester crosslinks between carboxylic acid groups and alcohol groups present on the CMC chemical backbone, and between carboxylic acid groups present on the CMC and alcohol groups present on the dexamethasone. Upon immersion into PBS, the CMC swells and the dexamethasone was observed to elute from the hydrogel, at a rate slower than in Example 35, due to chemical ester-bond formation between the dexamethasone and the CMC.

Example 37

This example describes the incorporation, with chemical crosslinking, of a bioactive species into the hydrogel material of a web material according to Example 28. Dexamethasone (Sigma, St. Louis) was dissolved at a concentration of 10 mg/100 ml in deionized water.

PVA was dissolved in the deionized water at a 10% concentration (i.e., 10 g/100 ml) using heat and stirring. Succinic acid (Sigma) was also dissolved in the PVA solution at a concentration of 2 g per 100 ml. Entrapped air was removed by centrifugation. The dexamethasone-PVA-succinic acid solution was then imbibed into a 7:1 web material (3.8 cm×10.2 cm) according to Example 5 using a roller to completely fill the void spaces of the highly porous web. The web material was air dried at room temperature for sixteen hours (16 hrs). The composite was placed in an oven set at one hundred forty degrees centigrade (140° C.) for fifteen (15) minutes to induce ester crosslinks between carboxylic acid groups present on the succinic acid and alcohol groups present on the PVA, and between carboxylic acid groups present on the succinic acid and alcohol groups present on the dexamethasone. In this manner, the dexamethasone was chemically linked via ester bonds to the succinic acid, which in turn was chemically linked via ester bonds to the PVA. Upon immersion into PBS, the PVA swelled and the dexamethasone was observed to elute from the hydrogel at a slow rate, due to ester bond formation between the dexamethasone and the succinic acid/PVA.

Example 38

This example describes the formation of an article of the present invention to include an added material in combination with a stretched bioabsorbable web. (FIG. 12).

A series of holes (0.5 cm) were cut in two rectangular pieces of solvent cast film composed of 85% d,l-PLA-co-15% PGA copolymer (available from Absorbable Polymers, Pelham, Ala., USA). A similarly sized rectangular piece of finished 6:1 web material according to Example 1 was obtained and placed between the two pieces of the film material and pressed together at elevated temperature and time sufficient to provide for both the softening and penetration of the PLA:PGA copolymer into the interstices of the Example 1 web. The resulting laminate composite possessed areas where the enclosed web material was regionally exposed by the film holes. Dependent on the applied pressure, temperature, and utilized film and web thicknesses, the porosity of the web between the opposing film layers may or may not become filled. Alternatively, the film, with or without holes, may be applied to a single surface of the provided web. When exposed to aqueous conditions at 37° C., the film component imparts a malleable stiffness that facilitates the web construct's tactile manipulation and maintenance in a desired non-planar form prior to implantation.

The composition of the described laminate component or components may be selected from either absorbable or non-absorbable natural or synthetic materials with desirable properties that may additionally act as carriers for bioactive agents, and may alternatively act as a media providing a controlled rate of release of the contained bioactive substance or substances. The described laminate composite may alternatively be affixed by various available means to other absorbable or non-absorbable natural or synthetic materials to elicit a biological response (e.g., haemostasis, inflammation), to provide for mechanical support, and/or as a vehicle for delivery of bioactive agents.

Example 39

Figure 10:
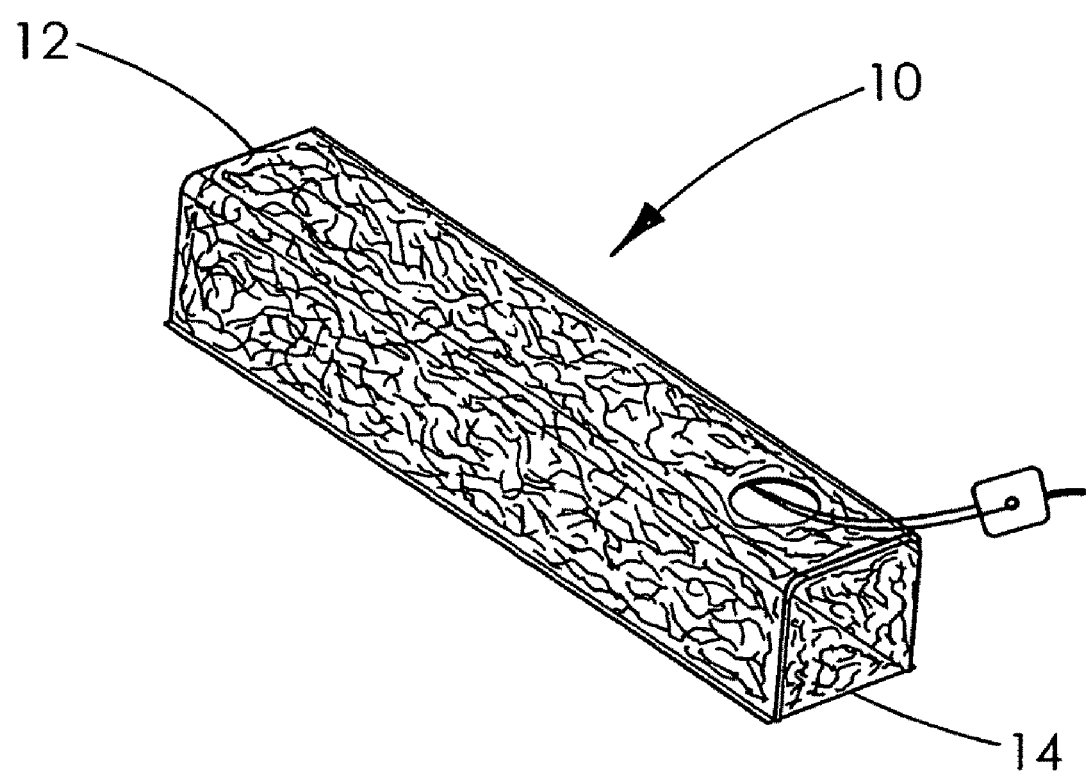
FIG. 10 is an illustration of a web material of the present invention attached to a pledget material.
Figure 10A:
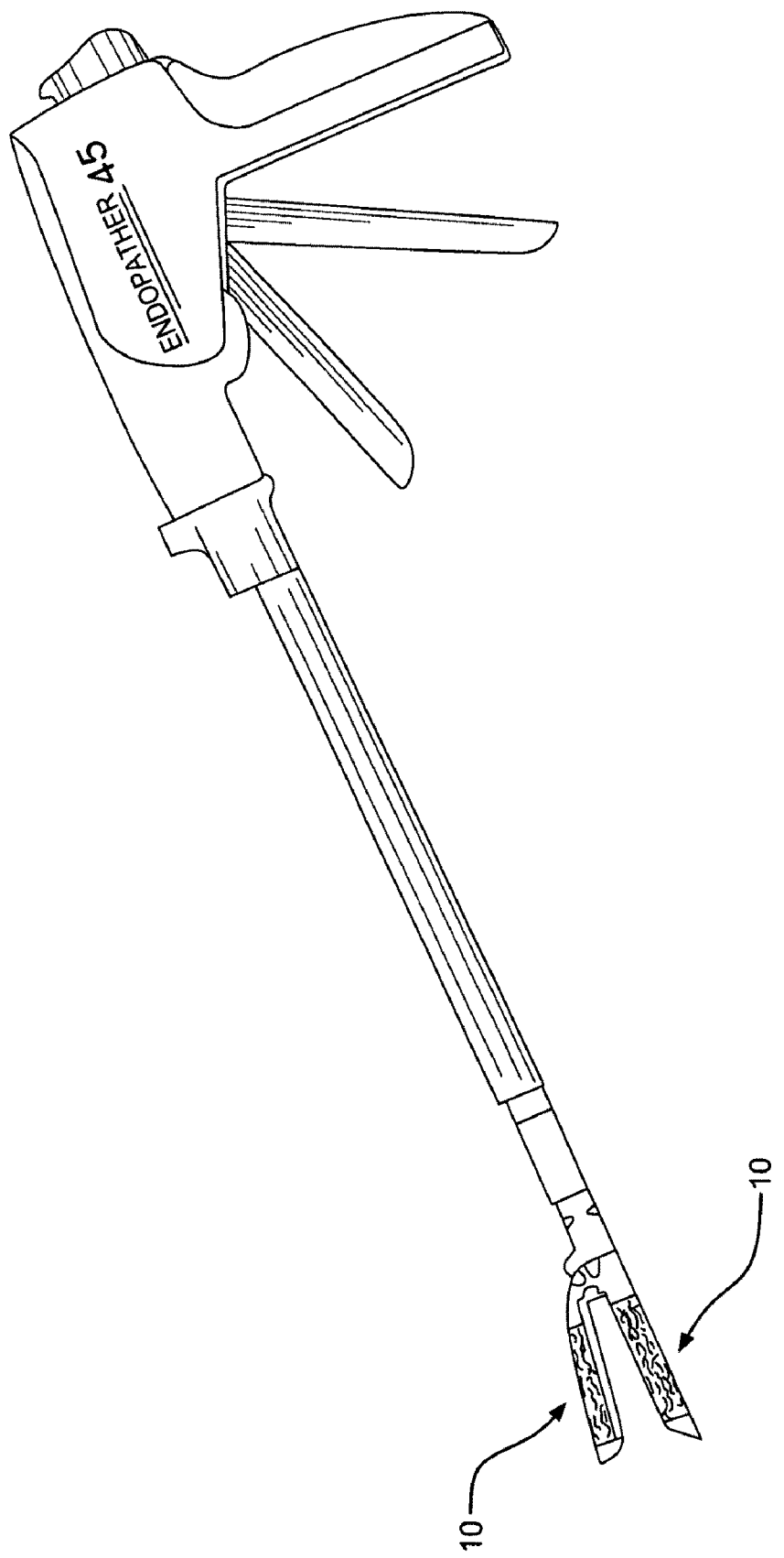
FIG. 10A is an illustration of a web material of the present invention attached to a pledget material and placed on a stapling apparatus.
Figure 10B:
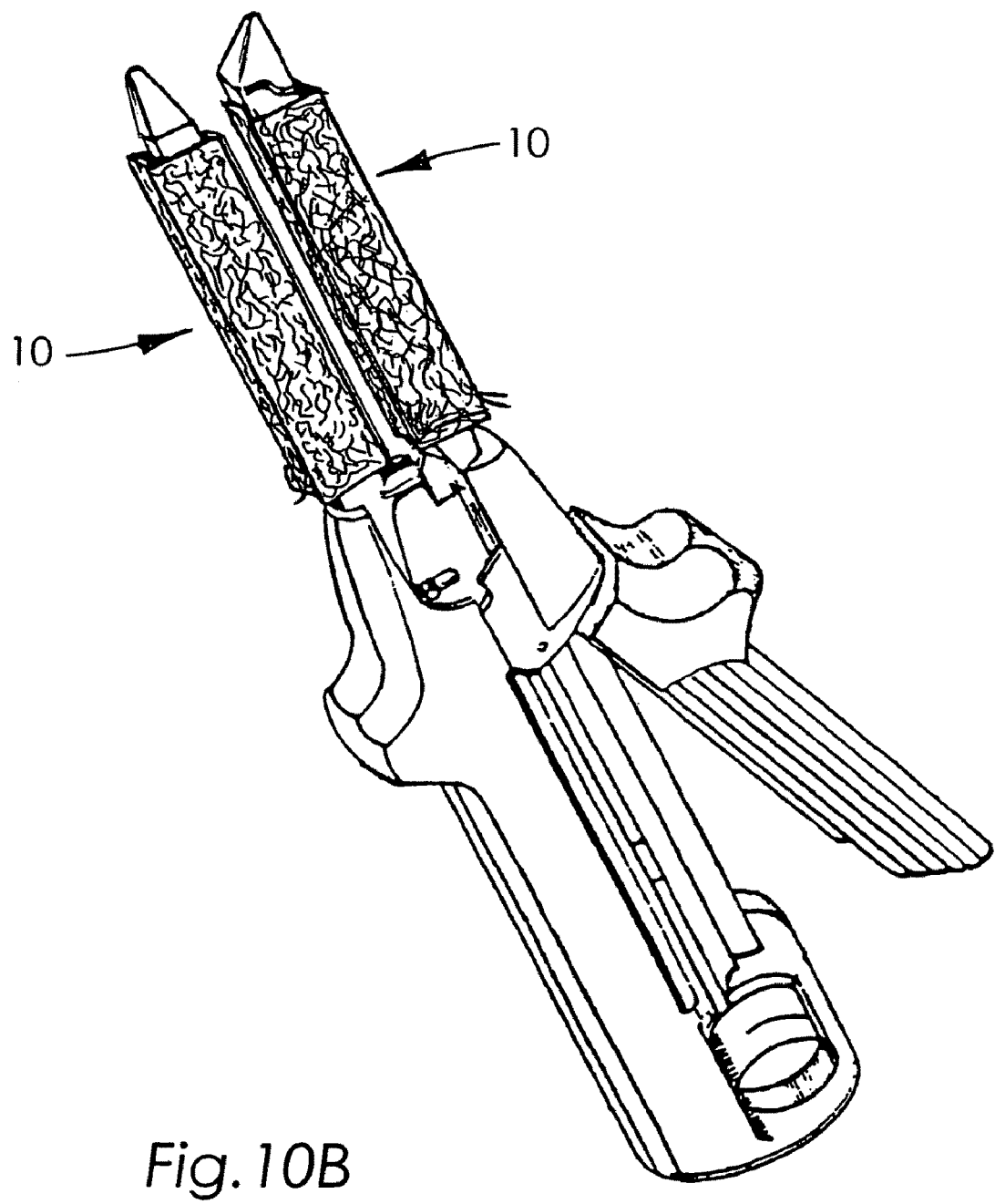
FIG. 10B is an illustration of a web material of the present invention attached to a pledget material and placed on a stapling apparatus.
Figure 11:
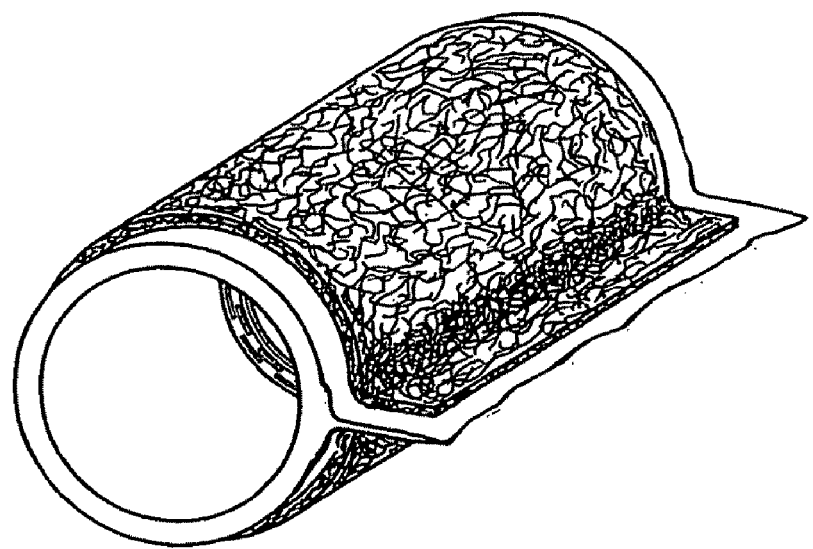
FIG. 11 is an illustration of a web material of the present invention in the form of an anastomotic wrap.

This example describes the construction of a composite material comprising a material of the present invention in combination with a pledget material (FIG. 10). The material of the present invention aids in holding the pledget material in place on a stapling apparatus during a surgical procedure (FIGS. 10A and 10B).

Two finished porous 6:1 stretched self-cohered web materials according to Example 1 were obtained, cut into similarly sized rectangular shapes with a pattern-following laser, and layered together to form a pouch between the layers. A pattern-following laser was also used to cut a rectangular-shaped bioabsorbable pledget material made of a block co-polymer of PGA:TMC (67:33 weight percent) obtained from W.L. Gore & Associates, Inc., Flagstaff, Ariz. The laser pattern controlled the exact dimensions of the three pieces of web material. The laser pattern also provided for four small alignment holes in the three pieces of web material. The alignment holes were used to locate the individual pieces on a mandrel and assist in welding the web materials together. The mandrel had a square cross-sectional shape.

To construct the device, the two layered piece of porous stretched web material was wrapped around three of the four sides of the mandrel and held in place with locating pins placed through the laser-cut holes. The pledget material was placed on the fourth side of the mandrel and held in place with locating pins placed through the laser-cut holes. Once the pieces were properly juxtaposed, the combination was inserted onto an ultrasonic welder and hot compression welds formed along the two long edges of the rectangular web materials to attach the porous stretched web material to the pledget material. The welds were approximately 0.025 cm in width. The final form of the construction was generally tubular in shape with a substantially square cross-section. The ultrasonic weld was sufficiently strong to hold the pledget material on the stapling apparatus during manipulation of the pledget material, while remaining sufficiently frangible to allow the pledget material and the porous stretched web material to separate when a pulling force is applied to the porous stretched web material.

To aid in separating the pledget material from the porous stretched web material, a pull cord made of polyethylene terephthalate (PET) was attached to the porous stretched web material prior to the above-recited ultrasonic welding process. A pull-tab was provided to the free end of the pull cord. Following construction of the composite material, the attached pull cord was coiled and stored in the pouch with the pull tab exposed.

In a similar embodiment, perforations were made in the pledget material adjacent to the ultrasonic welds to aid in separating the pledget material from the porous stretched web material.

Example 40

This example describes the construction of a composite material comprising a material of the present invention in combination with a non-bioabsorbable material (FIG. 15). In this embodiment, the bioabsorbable material occupies an area distinct from the non-bioabsorbable material of the composite. In particular, this composite material of the present invention is useful as an implantable dental device where the non-bioabsorbable portion of the device can remain in the body of an implant recipient, while the bioabsorbable portion disappears from the body of the implant recipient in a foreseeable time period. In this embodiment, a second implantable dental device can be placed in the area of the present invention originally occupied by the bioabsorbable portion of the invention.

A finished 6:1 web material according to Example 1 was obtained and cut into an oval shape approximately 0.5 cm wide×0.75 cm long. A rectangular piece of medical grade porous expanded polytetrafluoroethylene (ePTFE) with rounded corners was obtained from W.L. Gore & Associates, Inc., Flagstaff, Ariz. The ePTFE material was 0.75 cm wide and 1.0 cm long. A hole was cut in the ePTFE slightly smaller than the outer dimensions of the material of Example 1. The material of Example 1 was placed over the hole and solvent bonded in place using a small amount of a PLA:TMC/acetone solution applied along the edge of the hole sufficient to dissolve and flow some of the Example 1 material into the porous structure of ePTFE material. The utilized acetone solution was composed of an approximately 20% (w/v) poly(70% lactide-co-30% trimethylene carbonate), a copolymer commercially available from Boehringer Ingelheim, (Ingelheim, Germany and Petersburg, Va., USA). The composite material was briefly placed in a heated oven below the melting point of the material of Example 1 and under reduced pressure to fully remove the acetone solvent from the implantable medical device.

The device of this example is particularly suited for medical situations requiring regrowth, or regeneration, of tissue at the site of defect or injury. For example, in some dental applications, a space is created or enlarged in jawbone as part of a repair procedure. Unless surrounding gingival tissue is prevented from ingrowing the space, bone will not regrow in the space as desired. The device of this example is placed over the space in the bone to prevent unwanted tissues from ingrowing the space, while regrowth of desired bone tissue is fostered. With conventional devices made of ePTFE alone, the ePTFE remains permanently at the implantation site. In some situations, it may be desirable to place a second implantable dental device, such as a metallic stud, in the newly regrown bone tissue. Providing an ePTFE tissue barrier material with a bioabsorbable material according to the present invention would allow the bioabsorbable portion of the device to disappear from the implantation site and leave an unobstructed path through the ePTFE material to place a second dental implant.

Example 41

This example describes the construction of a composite material of the present invention having a non-bioabsorbable component combined with a bioabsorbable component (FIG. 21). In this example, a finished 6:1 bioabsorbable web material as described in Example 1 is bonded to a porous expanded polytetrafluoroethylene material to form an implantable sheet. The sheet can be used as a replacement, or substitute, for a variety of anatomical membranes. In particular, these membranes are useful as substitutes for dura and other membranes of the nervous system.

A bioabsorbable material according to Example 1 was obtained and overlaid on a thin ePTFE sheet material having delicate fibrils and spacious pore volumes. The ePTFE material was made according to U.S. Pat. No. 5,476,589 issued to Bacino, which is incorporated herein by reference.

The two sheets of material were solvent bonded together using the previously described PLA:TMC/acetone solution. Once bonded, the acetone was removed under heat and vacuum. The result was a composite sheet material suitable for use as an implantable medical device.

Example 42

This example describes the use of a porous, self-cohered, stretched web material of the present invention as an external supportive wrap for an anatomical structure or organ (FIG. 11). The wrap can also be used at an anastomotic site to minimize leakage and tissue adhesions.

In this example, a tissue compatibility study was performed in a group of animals. In the study, a piece of a porous, self-cohered, stretched web material made according to Example 1 was cut into a rectangular piece 2 cm×5 cm. The finished uni-axially 6:1 stretched web material of Example 1 exhibited an ability to elongate in the longer dimension of the web (i.e., 10 cm). A control material made from non-bioabsorbable materials was obtained from W.L. Gore & Associates, Inc., Flagstaff, Ariz. under the tradename PRECLUDE® Dura Substitute (PDS).

Two sites on each colon of eight (8) New Zealand White rabbits were used for the tests. At a distal site approximately 5 cm from the anus, a piece of one of the test materials was wrapped around the colon. Five centimeters further up the colon, more proximal, another piece of test material, different from the first piece, was wrapped around the colon. The materials formed sleeves around the serosa of the colon and were tacked in place with GORE-TEX® Sutures.

At the end of seven (7) days and thirty (30) days, all of the animals were sacrificed and the various materials retrieved intact. The particular segment of the wrapped colon with any accompanying adhesions were immersed in 10% neutral buffered formalin for paraffin histology. Adhesions to the materials were scored.

Upon gross evaluation and histologic analysis of the web material of the present invention showed incorporation of the web material in the serosa at seven (7) days. The web material of the present invention was well incorporated to the serosa of the colon as well as to the surrounding adhesions day thirty-one (31). The web material of the present invention was seen to be highly vascularized at both seven (7) and thirty-one (31) days. The PDS was not incorporated into the serosa at seven (7) or thirty-one (31) days nor had the material become vascularized.

The use of a web material of the present invention in combination with a coating of a bioabsorbable adhesion barrier material such as partially crosslinked polyvinyl alcohol (PVA), carboxymethylcellulose or hyaluronic acid biomaterial might be advantageous.

The invention claimed is:

1. An implantable article comprising melt-formed continuous filaments intermingled to form a porous web wherein said filaments are self-cohered to each other at multiple contact points, wherein said filaments comprise at least one semi-crystalline polymeric component covalently bonded to or blended with at least one amorphous polymeric component, wherein said filaments possess partial to full polymeric component phase immiscibility when in a crystalline state, wherein said porous web has a percent porosity greater than ninety, wherein twenty (20) percent to forty (40) percent of said filaments have a diameter larger than twenty (20) microns, wherein said filaments have a mean diameter of from sixteen (16) to twenty (20) microns, and a hydrogel material placed on at least one of said filaments.

2. The implantable article of claim 1 wherein the hydrogel is cross-linked.

3. The implantable article of claim 2 wherein said hydrogel material comprises polyvinyl alcohol.

4. The implantable article of claim 2 wherein said hydrogel material comprises carboxymethylcellulose.

5. The implantable article of claim 2 wherein said hydrogel material comprises a co-polymer of polyethylene glycol and polypropylene glycol.

6. The implantable article of claim 2 further comprising a bioactive species in combination with the cross-linked hydrogel material.

7. The implantable article of claim 6 wherein the bioactive species comprises an anti-inflammatory.

8. The implantable article of claim 7 wherein the anti-inflammatory is dexamethasone.

9. The implantable article of claim 1 wherein said hydrogel material fills at least part of at least one void space present between said filaments.

10. The implantable article of claim 9 wherein the hydrogel is cross-linked.

11. The implantable article of claim 9 wherein said hydrogel material comprises polyvinyl alcohol.

12. The implantable article of claim 9 wherein said hydrogel material comprises carboxymethylcellulose.

13. The implantable article of claim 9 wherein said hydrogel material comprises a co-polymer of polyethylene glycol and polypropylene glycol.

14. The implantable article of claim 9 further comprising a bioactive species in combination with the hydrogel material.

15. The implantable article of claim 14 wherein the bioactive species comprises an anti-inflammatory.

16. The implantable article of claim 15 wherein the anti-inflammatory is dexamethasone.

17. The implantable article of claim 10 wherein said hydrogel material comprises polyvinyl alcohol.

18. The implantable article of claim 10 wherein said hydrogel material comprises carboxymethylcellulose.

19. The implantable article of claim 10 wherein said hydrogel material comprises a co-polymer of polyethylene glycol and polypropylene glycol.

20. The implantable article of claim 10 further comprising a bioactive species in combination with the cross-linked hydrogel material.

21. The implantable article of claim 20 wherein the bioactive species comprises an anti-inflammatory.

22. The implantable article of claim 21 wherein the anti-inflammatory is dexamethasone.

23. The implantable article of claim 1 wherein said implantable article has a percent porosity greater than ninety-one absent inclusion of any fillers or other added components that may effectively reduce said porosity.

24. The implantable article of claim 1 wherein said hydrogel material comprises polyvinyl alcohol.

25. The implantable article of claim 1 wherein said hydrogel material comprises carboxymethylcellulose.

26. The implantable article of claim 1 wherein said hydrogel material comprises a co-polymer of polyethylene glycol and polypropylene glycol.

27. The implantable article of claim 1 further comprising a bioactive species in combination with the hydrogel material.

28. The implantable article of claim 27 wherein the bioactive species comprises an anti-inflammatory.

29. The implantable article of claim 28 wherein the anti-inflammatory is dexamethasone.

30. An implantable article comprising melt-formed continuous filaments intermingled to form a porous web wherein said filaments are self-cohered to each other at multiple contact points, wherein said filaments comprise a first semi-crystalline polymeric component covalently bonded to or blended with at least one additional semi-crystalline polymeric component, wherein said filaments possess partial to full polymeric component phase immiscibility when in a crystalline state, wherein said porous web has a percent porosity greater than ninety, wherein twenty percent to forty percent of said filaments have diameters larger than twenty microns, wherein said filaments have a mean diameter of from sixteen (16) to twenty (20) microns, and a hydrogel material placed on at least one of said filaments.

31. The implantable article of claim 30 wherein the hydrogel material is cross-linked.

32. The implantable article of claim 31 wherein said hydrogel material comprises polyvinyl alcohol.

33. The implantable article of claim 30 wherein said hydrogel material comprises carboxymethylcellulose.

34. The implantable article of claim 31 wherein said hydrogel material comprises polyvinyl alcohol.

35. The implantable article of claim 31 wherein said hydrogel material comprises carboxymethylcellulose.

36. The implantable article of claim 31 wherein said hydrogel material comprises a co-polymer of polyethylene glycol and polypropylene glycol.

37. The implantable article of claim 36 further comprising a bioactive species in combination with the cross-linked hydrogel material.

38. The implantable article of claim 37 wherein the bioactive species comprises an anti-inflammatory.

39. The implantable article of claim 38 wherein the anti-inflammatory is dexamethasone.

40. The implantable article of claim 30 wherein said hydrogel material fills at least part of at least one void space present between said filaments.

41. The implantable article of claim 40 wherein the hydrogel material is cross-linked.

42. The implantable article of claim 40 wherein said hydrogel material comprises polyvinyl alcohol.

43. The implantable article of claim 40 wherein said hydrogel material comprises carboxymethylcellulose.

44. The implantable article of claim 40 wherein said hydrogel material comprises a co-polymer of polyethylene glycol and polypropylene glycol.

45. The implantable article of claim 30 wherein the percent porosity is greater than ninety-one absent inclusion of any fillers or other added components that may effectively reduce said porosity.

46. The implantable article of claim 30 wherein said hydrogel material comprises a co-polymer of polyethylene glycol and polypropylene glycol.

47. The implantable article of claim 30 further comprising a bioactive species in combination with the hydrogel material.

48. The implantable article of claim 47 wherein the bioactive species comprises an anti-inflammatory.

49. The implantable article of claim 48 wherein the anti-inflammatory is dexamethasone.

* * * * *